US007947467B2

(12) United States Patent
Kritzman et al.

(10) Patent No.: US 7,947,467 B2
(45) Date of Patent: *May 24, 2011

(54) METHODS FOR MONITORING PATHOLOGICAL CONDITIONS IN A FEMALE SUBJECT

(75) Inventors: Amnon Kritzman, Zichron Yaakov (IL); Nitsa G. Nachshon, Kibbutz Geva (IL); Yael Behar, Moshav Ein Ayala (IL); David Brusilovsky, Herzliya (IL); Menashe Terem, Yavne (IL); Adva Brand, Benyamina (IL)

(73) Assignee: Common Sense Ltd., Caesarea (IL)

( * ) Notice: Subject to any disclaimer, the term of this patent is extended or adjusted under 35 U.S.C. 154(b) by 97 days.

This patent is subject to a terminal disclaimer.

(21) Appl. No.: 12/472,653

(22) Filed: May 27, 2009
(Under 37 CFR 1.47)

(65) Prior Publication Data
US 2010/0136707 A1 Jun. 3, 2010

Related U.S. Application Data

(63) Continuation-in-part of application No. 11/949,541, filed on Dec. 3, 2007, now Pat. No. 7,541,177, which is a continuation of application No. 11/105,438, filed on Apr. 14, 2005, now Pat. No. 7,314,752, which is a continuation-in-part of application No. 10/285,499, filed on Nov. 1, 2002, now Pat. No. 6,921,647, which is a continuation-in-part of application No. PCT/IL02/00588, filed on Jul. 18, 2002, which is a continuation of application No. 11/541,198, filed on Sep. 28, 2006, now abandoned, and a continuation-in-part of application No. 09/907,926, filed on Jul. 19, 2001, now Pat. No. 6,627,394.

(60) Provisional application No. 60/365,684, filed on Mar. 18, 2002, provisional application No. 60/749,043, filed on Dec. 12, 2005, provisional application No. 60/778,840, filed on Mar. 6, 2006.

(51) Int. Cl.
*C12Q 1/58* (2006.01)
(52) U.S. Cl. ......................................... 435/12; 604/358
(58) Field of Classification Search .................... 435/12; 604/358
See application file for complete search history.

(56) References Cited

U.S. PATENT DOCUMENTS

| 2,664,879 | A | 1/1954 | Hardy ................................. 128/2 |
| 3,427,225 | A | 2/1969 | Harvill ........................ 195/103.5 |
| 3,509,872 | A | 5/1970 | Truhan ................................ 128/2 |
| 4,029,597 | A | 6/1977 | Neisius et al. .................. 252/408 |
| 4,029,598 | A | 6/1977 | Neisius et al. .................. 252/408 |
| 4,266,022 | A | 5/1981 | Lamprecht ...................... 435/26 |
| 4,532,216 | A | 7/1985 | Wang ................................ 436/2 |
| 4,666,833 | A | 5/1987 | Roy et al. ........................ 435/26 |
| 5,063,930 | A | 11/1991 | Nucci ............................. 128/632 |
| 5,094,955 | A | 3/1992 | Calandra et al. ............... 435/291 |
| 5,217,444 | A | 6/1993 | Schoenfeld .................... 604/361 |
| 5,252,459 | A | 10/1993 | Tarcha et al. ..................... 435/6 |
| 5,275,591 | A | 1/1994 | Mavinkurve ................... 604/387 |
| 5,304,648 | A | 4/1994 | Chen .............................. 544/410 |
| 5,312,591 | A | 5/1994 | Doi ................................. 422/56 |
| 5,384,411 | A | 1/1995 | Robotti et al. .................. 549/31 |
| 5,425,377 | A | 6/1995 | Caillouette .................... 128/759 |
| 5,445,147 | A | 8/1995 | Schoendorfer et al. ....... 128/632 |
| 5,459,078 | A | 10/1995 | Kline et al. ..................... 436/518 |
| 5,468,236 | A | 11/1995 | Everhart et al. ................ 604/361 |
| 5,660,790 | A | 8/1997 | Lawrence et al. ............... 422/56 |
| 5,823,953 | A | 10/1998 | Roskin et al. .................. 600/367 |
| 5,823,954 | A | 10/1998 | Chaffringeon ................ 600/367 |
| 5,853,669 | A | 12/1998 | Wolfbeis ..................... 424/82.05 |
| 5,876,389 | A | 3/1999 | Bouchard et al. ........... 604/385.1 |
| 5,897,834 | A | 4/1999 | Lawrence et al. ............... 422/56 |
| 5,910,447 | A | 6/1999 | Lawrence et al. ............. 436/111 |
| 5,925,318 | A | 7/1999 | Kruzel et al. .................. 600/309 |
| 6,099,801 | A | 8/2000 | Lawrence et al. ............... 422/56 |
| 6,106,461 | A | 8/2000 | Roskin et al. .................. 600/309 |
| 6,126,597 | A | 10/2000 | Smith et al. .................... 600/362 |
| 6,149,590 | A | 11/2000 | Smith et al. .................... 600/367 |
| 6,200,817 | B1 | 3/2001 | Lawrence ..................... 436/111 |
| 6,203,496 | B1 | 3/2001 | Gael et al. ..................... 600/362 |
| 6,395,955 | B1 | 5/2002 | Roe et al. ...................... 604/361 |
| 6,426,227 | B1 | 7/2002 | Kritzman et al. ............... 436/43 |
| 6,562,297 | B1 | 5/2003 | Bonstein et al. ................. 422/56 |
| 6,610,904 | B1 | 8/2003 | Thomas et al. ................. 604/383 |
| 6,627,394 | B2 * | 9/2003 | Kritzman et al. ................. 435/4 |
| 6,627,790 | B2 | 9/2003 | Bouchard et al. ............. 604/383 |
| 6,689,114 | B2 | 2/2004 | Bouchard et al. ........ 604/385.14 |
| 6,719,691 | B2 | 4/2004 | Kritzman et al. .............. 600/362 |
| 6,921,647 | B2 * | 7/2005 | Kritzman et al. ................ 435/12 |
| 7,314,752 | B2 * | 1/2008 | Kritzman et al. ........... 435/288.7 |
| 7,541,177 | B2 * | 6/2009 | Kritzman et al. ........... 435/288.7 |
| 2001/0025140 | A1 | 9/2001 | Torok et al. .................... 600/367 |
| 2003/0120180 | A1 | 6/2003 | Kaylor et al. .................. 600/584 |
| 2003/0166293 | A1 | 9/2003 | Kritzman et al. .............. 436/111 |
| 2006/0127929 | A1 | 6/2006 | Swager et al. ..................... 435/6 |
| 2007/0003993 | A1 | 1/2007 | Kritzman et al. ................ 435/12 |
| 2007/0073192 | A1 | 3/2007 | Caillouette .................... 600/584 |
| 2007/0134740 | A1 * | 6/2007 | Brusilovsky et al. ......... 435/7.22 |
| 2008/0086060 | A1 | 4/2008 | Kritzman et al. .............. 600/584 |

FOREIGN PATENT DOCUMENTS

| DE | 199 14 037 A1 | 9/2000 |
| DE | 100 16 383 A1 | 6/2001 |
| EP | 0 586 590 B1 | 3/1994 |
| GB | 2 353 357 A | 2/2001 |
| WO | WO 2005/093414 A2 | 10/2005 |

OTHER PUBLICATIONS

Mish, F.C. Ed., Merriam-Webster's Collegiate Dictionary, 1993, Merriam-Webster, Inc., Tenth Edition, p. 1139.

* cited by examiner

*Primary Examiner* — Ralph Gitomer
(74) *Attorney, Agent, or Firm* — Winston & Strawn LLP

(57) ABSTRACT

A method for identifying physiological conditions associated with the pH or the buffer capacities of biological fluid secreted from a person, by providing a secretion-monitoring article of a body that includes an absorbent material for absorbing a biological fluid secreted from a person and an indicator system having a hydrophobic chemical composition that includes an indicator agent and an ion-balance reagent, at specific relative amounts. Optionally, a competitive agent for establishing a pre-set threshold of an analyte of interest in a tested bodily fluid, is added to the indicator system, wherein the indicator reagent being charged oppositely to the analyte of interest and the competitive reagent having the same charge as the indicator reagent.

20 Claims, 8 Drawing Sheets

METHODS FOR MONITORING PATHOLOGICAL CONDITIONS IN A FEMALE SUBJECT

CROSS-REFERENCE TO RELATED APPLICATIONS

This application is (A) a continuation-in-part of U.S. application Ser. No. 11/949,541, filed Dec. 3, 2007 now U.S. Pat. No. 7,541,177, which in turn is a continuation of U.S. application Ser. No. 11/105,438, filed Apr. 14, 2005, now U.S. Pat. No. 7,314,752, which in turn is a continuation-in-part of U.S. application Ser. No. 10/285,499, filed Nov. 1, 2002, now U.S. Pat. No. 6,921,647, which in turn is a continuation-in-part of the U.S. national stage of International Application PCT/IL02/00588, filed Jul. 18, 2002, which International Application claims the benefit of U.S. Provisional Application No. 60/365,684, filed Mar. 18, 2002; and (B) is a continuation of U.S. application Ser. No. 11/541,198, filed Sep. 28, 2006 now abandoned, which claims the benefit of U.S. Provisional Applications Nos. 60/749,043 filed Dec. 12, 2005 and 60/778,840 filed Mar. 6, 2006.

Also, U.S. application Ser. No. 10/285,499, filed Nov. 1, 2002, now U.S. Pat. No. 6,921,647, is a continuation-in-part of U.S. application Ser. No. 09/907,926, filed Jul. 19, 2001, now U.S. Pat. No. 6,627,394.

The entire content of each earlier application is expressly incorporated herein by reference thereto.

TECHNICAL FIELD

The present invention relates to the field of medical diagnostics and more specifically, to an improved identification of secreted biological fluids using a secretion-monitoring article to identify amniotic fluid, secretions associated with bacterial, parasite, fungal, or yeast infections even in the presence of interfering biological fluids or to determine dehydration. The present invention also relates to improved methods for reducing the incidence of false positive detection. Furthermore, the present invention also provides improved method for determining the presence of a given analyte, above a pre-set threshold.

BACKGROUND OF THE INVENTION

Many bodily fluids can be identified by chemical properties such as pH. One exceptionally useful method of determining the pH of a liquid sample is through the use of an indicator, a chemical compound or combination of compounds, that has a pH dependent color. Well known examples include tea and wine. General details and descriptions of some indicators can be found, for example, in "Indicators," E. Bishop, Pergamon Press, 1972, chapter 3.

Often an indicator is attached to a solid substrate such as paper. A sample of a liquid of which the pH needs to be determined is applied to the substrate. The pH of the liquid is determined by the color of the indicator present on the substrate. Depending on how the indicator is attached to the substrate, application of the liquid sample may cause the indicator to leach out of the substrate. Indicator leaching is undesirable and so the indicator is often substantially immobilized on the substrate.

Analytical procedures and devices for diagnosing medical conditions are commonly employed in assays comprising means for determining the presence and/or concentration of analytes of interest in bodily fluids with chemically reactive means adapted to provide a visual indication as a result of interacting with biological fluids, and disposable absorbent products comprising same, e.g., U.S. Pat. Nos. 4,266,022; 5,445,147 and 6,203,496. The visual indication provided by these absorbent products is not made to distinguish between indication for a substance of interest and the indication from interfering fluids, particularly, urine. Moreover, some of the articles disclosed and claimed in the aforementioned patents are directed to indicate the presence or absence of specific anlaytes in urine, e.g. for the purpose of determining dehydration as disclosed in U.S. Pat. No. 6,203,496, and thus cannot be applied also for determining medical conditions in vaginal secretions.

Various medical conditions can be diagnosed by identifying the chemical and physical properties of a vaginal secretion, such as, salts of volatile amines as disclosed in U.S. Pat. No. 6,099,801. Identifying the pH of the secretions also indicates the presence of medical conditions. U.S. Pat. Nos. 5,660,790 and 5,910,447 disclose test devices for analyzing the pH of an aqueous liquid sample, however, the pH range identified by these devices is extremely narrow, namely 4.6-4.8. Moreover, the pH indicator composition is hydrophilic and thus cannot readily retain a stable indication, particularly indications requiring dehydrated environment. U.S. Pat. No. 5,468,236 discloses a disposable absorbent product comprising a chemically reactive means adapted to provide a visual indication as a result of interacting with biological fluids. The properties of the chemical means however are not defined. Moreover, the visual indication is not adapted to provide a distinct indication for a desired substance in the presence of interfering fluids.

A number of devices involving panty shields with pH indicators are known in the art, for example in U.S. Pat. Nos. 5,217,444; 5,823,953; 6,106,461 and 6,689,114. These devices can be worn by the user and whenever there is a secretion it is immediately detected by the pH indicator. U.S. Pat. No. 6,562,297 discloses an indicator bound to a hydrophilic synthetic membrane substrate and a device, such as a panty shield with an indicator bound to hydrophilic synthetic membrane substrate. A general problem, however, with these pH indicators is that they often provide "false positives" due to changes in pH on drying, interfering biological fluids and repetitive cycles of drying/wetting. Often a vaginal secretion cannot be identified with absolute certainty by an indicator due to the existence of a plurality of fluids collected with a similar pH. The "false positive" readings can be stressful and time consuming to the user. A device that minimizes these "false positive" readings is needed.

False positive readings can be caused, for example, by interfering biological fluids, such as urine. Vaginal secretions of a patient with vaginosis have a pH between 4.7 and 6.5. Because urine of a healthy patient has a pH between 5.0 and 8.0, it is very difficult to diagnose a secretion as arising from vaginosis with a high degree of confidence by just using a pH based indicator test. One solution known in the art is to sample fluid from within the vagina, where urine is not ordinarily found. This is uncomfortable and requires a visit to a health-care professional.

Another known solution for the problem of 'false positive' indications commonly associated with diagnostic methods, is providing a competitive agent having a stronger affinity to the analyte than to the indicator reagent. U.S. Pat. No. 5,459,078 (the '078 patent) discloses a digoxin assay employing a capture reagent and an indicator agent. However, the capture agent of the '078 patent differs from the competitive reagent of the present invention in that it binds to both the analyte and the indicator (see col. 10, ll.11-12 of the '078 application) while the competitive agent of the present invention only binds to the analyte. Thus, unlike in the present invention, there is no competition between the capture agent and the indicator for the analyte in the assay of the '078 patent, which is crucial feature in the present invention for avoiding "false positives". Moreover, there is no teaching or suggestion in the '078 patent regarding the determination of the pre-set threshold of a visible indication by the concentration of the competitive agent.

In addition, U.S. Pat. No. 5,252,459 (the '459 patent) discloses a competitive assay in which an indicator reagent and the analyte compete for binding to the capture reagent (see col. 7, ll. 53-56 of the '459 patent). Thus, unlike in the present invention, there is no competition between the capture agent and the indicator for the analyte in the assay of the '459 patent, which is crucial feature in the present invention for avoiding "false positives". Moreover, there is no teaching or suggestion in the '459 patent regarding the determination of the pre-set threshold of a visible indication by the concentration of the competitive agent.

Furthermore, US 2006/0127929 generally relates to organic polymers able to participate in an analyte-recognition process, where an analyte facilitates an energy transfer between the polymer and the indicator or otherwise affects the interaction between the polymer and the indicator. This reference is completely different from the present invention since it does not relate to competitive assays at all.

European Patent No. 586 590 discloses binding assays for determining the presence or amount of an analyte of interest in a test sample, using a binding pair, such as an antibody and an antigen, a capture reagent comprising the first member of the binding pair, an indicator containing the second member of the binding pair and a detectable label and a solid phase material containing a polymeric cation reaction site. The assays of EP 586 590 are limited to immunoassay formats.

WO 2005/093414 discloses an assay device for detecting the presence or absence of amines within a test sample comprising a fluidic medium that defines a detection zone, wherein a chemichromic dye, comprising arylmethanes is contained within said detection zone, said chemichromic dye being capable of undergoing a detectable color change upon reaction with one or more amines.

A second example for a medical condition that can be diagnosed by identifying the chemical and physical properties of a vaginal secretion is amniotic fluid leaking from the vagina of a pregnant woman.

U.S. Pat. No. 6,126,597 (the '597 patent) and U.S. Pat. No. 6,149,590, (the '590 patent) a continuation-in-part of the '597 patent, are directed to a device in the form of a sanitary napkin with a pH indicator configured to identify the presence of amniotic fluid in a vaginal secretion. The '597 and '590 patents are subject to the problem of giving false positive results. The device of the '590 patent addresses this problem by further including in the device a microscope visualizable slide configured to gather a portion of a vaginal secretion. If the indicator shows the pH corresponding to that of amniotic fluid, the user presents a health-care professional with the slide. The health-care professional examines the slide with the help of a microscope for the typical fern-shaped patterns indicative of the presence of amniotic fluid.

There are a couple of disadvantages associated with this device. First, it requires that the patient visits the health-care professional to distinguish between positive and false-positives and second, a significant amount of time is lost in having the slide viewed by a professional to determine if amniotic fluid is actually leaking.

U.S. Pat. No. 5,897,834 discloses a device useful in a clinical setting for the differentiation between urine and vaginal secretions associated with vaginosis or urine and amniotic fluid. The device includes the use of indicators with a negatively charged group immobilized to a solid polymer substrate containing quaternary ammonium groups. Further the device includes a gaseous amine-releasing reagent and an amine indicator. The use of the polymer substrate containing quaternary ammonium groups is disclosed to have an advantage of sharpening the pH dependent color transition. However, these polymer substrates have been found to be less useful in non-clinical settings: the indicated pH of dried vaginal secretions is low enough to be misdiagnosed as indicating vaginosis. Thus although the device disclosed in U.S. Pat. No. 5,897,834 is useful in a clinical setting where the health care professional applies the vaginal secretion to the device and observes the color change, if integrated in a patient useable device, such as a panty shield, the device gives abundant false positive results.

There is a need for an indicator system that can differentiate between a specific biological fluid of interest and an interfering biological fluid, such as, urine. Further there is a need for a device that can distinguish between normal vaginal secretions and those associated with amniotic fluid leakage or vaginosis. Further, a system in which false positive results are minimized and a reliable indication is stable over time, while reducing the amount of time required to get the reliable result is also needed. Such a system is ideally useable by the patient to lead to greater peace of mind and to minimize unnecessary hospital visits. The characteristics of such an indicator system must not change due to long use or as a result of a wetting drying cycle and must distinguish between interfering biological fluids and minimize false positive readings. In addition there is a need for a bodily fluid-testing composition capable of identifying an ion concentration exceeding a pre-set specific threshold in tested bodily fluids, and at the same time capable at differentiating between a specific bodily fluid of interest and an interfering bodily fluid. The present invention now overcomes these problems and satisfies these needs.

SUMMARY OF THE INVENTION

The present invention overcomes the disadvantages of the prior art by the use of an indicator system integrated into various self useable products thereby providing highly specific and highly sensitive diagnostic indications, with minimal "noise" (interference) from nonspecific binding of interfering substances. Specificity and sensitivity of the indicator system is achieved by the unique relative amounts of the major ingredients in the system, namely, at least one indicator agent and at least one ion balance reagent. The invention further provides a solution to the problem of "false positives" commonly associated with assays known in the art, by providing an indicator system that further comprises a competitive reagent having a stronger binding affinity to the analyte than the at least one indicator reagent. As the concentration of the competitive reagent determines the pre-set threshold of a visible indication, the analyte in a concentration above the pre-set threshold can be readily and accurately detected by the change of the color of the composition. These key elements are not taught or suggested by any of the cited references. Generally, the indicator system is integrated within an article comprising an absorbent material for absorbing a biological fluid secreted from a person and the indicator system.

Preferably, the indicator system has a hydrophobic chemical composition comprising at least one indicator agent and at least one ion-balance reagent. The indicator system is associated with the absorbent material such that the biological fluids absorbed by the absorbent material further contact the indicator system so that a reliable indication of the pH and/or buffer capacity of that fluid can be obtained, wherein a positive indication remains detectable for at least 48 hours, and preferably at least 72 hours.

Upon the addition of a competing reagent to the indicator system, the method of the present invention is capable of offering improved accuracy of detection and analysis. Without wishing to be bound by any particular theory or mechanism of action, the competing substance competes with an indicator reagent in order to compensate for variability in specific binding of the analyte with said indicator. Thus, the ability of the compositions of the invention to detect a specific ion concentration, above or below a pre-set threshold, is determined by the concentration of the competitor.

The method can be used by the user in many forms of indicator systems. It is preferable, however, that the indicator systems is integrated in an article that is in the form of a swab, gauze, panty shield, hygienic napkin, a diaper or interlabial absorbent structure. Furthermore, any user, male or female, young or old, can use the article. The particular examples of the invention as presented herein are not intended to limit the scope of the invention, but simply to illustrate and represent the numerous potential forms in which the invention can be used.

Unexpectedly, indications corresponding to pathological conditions, such as, bacterial vaginosis and amniotic fluids, are stable and remain indicative for at least 48 hours.

Advantageously, the indicator system has a chemical composition that reacts with biological fluids containing protonated amine cations differently than with bodily fluids that do not contain protonated amine cations.

Preferably, the article has a mounting means for positioning the absorbent body to receive the fluids secreted during the normal activity of the user, such mounting means being, for example, an adhesive strip or other attachment member.

Typically, the indicator system is associated with the absorbent material such that the biological fluids contact the indicator system while being worn.

Further, the invention provides a method of attaching an indicator, or a plurality of indicators, to a substrate. The substrate can be made of many materials, for example, polypropylene, paper or cotton, polyester membranes and can be of many structures including of a membrane, fabric, mesh, gauze, thread, fiber and a sheet. A mixture comprising a pre-formed polymer (such as cellulose), a plasticizer, a wetting agent, at least one ion-balance reagent and at least one indicator is prepared. In some embodiments, a solvent is added to the mixture. The mixture is applied to a substrate for example by dipping the substrate in the mixture or by spraying or spreading the mixture onto the substrate. The substrate with the applied mixture is allowed to dry. When dry, the at least one indicator is bound to the substrate with the help of the polymer. This method is exceptionally useful when the indicators have a substantially negatively charged functional group such as an acetate or a sulfonate.

There is also provided according to the teachings of the present invention an additional method of making a diagnostic article comprising of the steps of attaching an indicator to a substrate, especially a neutral substrate, by applying a surfactant solution to the substrate and letting it dry, preferably under vacuum, then once the surfactant is dry, an indicator solution or a solution with a reagent is applied to the substrate and allowed to dry, preferably under vacuum, wherein the at least one indicator to be attached to the substrate preferably is a substantially negatively charged functional group with a cationic surfactant. The method further comprises placing the at least one indicator in association with an absorbent body.

According to one aspect, the present invention provides a method of identifying a pathological condition in a subject which comprises:

positioning a secretion-monitoring article to receive a biological fluid secreted from the subject, the secretion-monitoring article comprising a body that includes an absorbent material for absorbing the biological fluid and an indicator system having a hydrophobic chemical composition comprising at least one indicator agent and at least one ion-balance reagent which is a quaternary amine, wherein the indicator system provides an indication of physiological conditions associated with a pH or a buffer capacity of the biological fluid, which indication is stable and remains indicative for at least 48 hours; and viewing the article within the at least 48 hour period to identify the pathological condition based on the indication determined by the indicator system, wherein the amount of the at least one indicator agent does not exceed about 2% and the amount of the at least one ion-balance reagent does not exceed about 5% wherein the percents are weight percent based on the total weight of the indicator system and the total weigh of the mixture equals 100%.

According to one embodiment, the molar ratio of the at least one ion-balance reagent to the at least one indicator agent is within the range of 3:1 to 10:1. According to a preferred embodiment, the at least one ion-balance reagent to the at least one indicator agent is within the range of 4:1 to 9:1.

According to another embodiment, the indicator system further comprises a pre-formed polymer and a plasticizer.

According to yet another embodiment, the at least one ion-balance reagent is in an amount of about 1% to 6% and the at least one indicator agent is in an amount of about 0.1% to 2%, wherein the percents are weight percent based on the total weight of the composition and the total weight of the composition equals 100%.

According to an alternative embodiment, the indicator system further comprises a wetting agent polymer.

According to yet another embodiment, the pre-formed polymer is in an amount of about 30% to 50%; the plasticizer is in an amount of about 20% to 30%; the wetting agent is in an amount of about 20% to 35%; the at least one ion-balance reagent is in an amount of about 1% to 6% and the at least one indicator agent is in an amount of about 0.1% to 2%, wherein the percents are weight percent based on the total weight of the composition and the total weight of the composition equals 100%.

According to yet another embodiment, the pre-formed polymer is in an amount of about 33% to 45%; the plasticizer is in an amount of about 24% to 28%; the wetting agent is in an amount of about 24% to 34%; the ion-balance reagent is in an amount of about 2% to 5% and the indicator agent is in an amount of about 0.3% to 1%, wherein the percents are weight percent based on the total weight of the composition and the total weight of the composition equals 100%.

According to yet another embodiment, the indicator system further comprises a competitive reagent having the same charge as the indicator reagent wherein the binding affinity of the competitive reagent to the analyte is stronger than the binding affinity of the indicator reagent to said analyte, and wherein the concentration of the competitive reagent determines a pre-set threshold of a visible indication such that upon contact of the composition with a bodily fluid comprising said analyte in a concentration above the pre-set threshold, said composition provides an indication of physiological conditions associated with the pH or the buffer capacities of the bodily fluid.

According to yet another embodiment, the competitive reagent is in an amount of about 0.2% to 8%; preferably, about 0.4% to 5%.

According to yet another embodiment, the competitive reagent is selected from the group consisting of: citric acid, oxalic acid, tartaric acid, succinic acid, glutaric acid, lactic acid, pyruvic acid, hydroxypropionic acid, hydroxyvaleric acid, adipic acid, suberic acid, orotic acid, phthalic acid, 2-[(2-hydroxy-1,1-bis(hydroxymethyl)ethyl)amino]ethanesulfonic acid, 4-(2-hydroxyethyl)piperazine-1-ethanesulfonic acid, cyclodextrine sulfate, dextran sulfate, and carboxymethyl cellulose.

According to yet another embodiment, the pKa of the at least one indicator agent is lower than the pH of the biological fluid, said pH is determined by a physiological condition. According to yet another embodiment, the indicator agent is negatively charged. According to yet another embodiment the indicator agent is a weak acid. Preferably the indicator agent is a negatively charged functional group selected from acetate and sulfonate. In a preferred embodiment, the indicator agent is selected from the group consisting of: cresol red, alizarin, bromcresol purple, chlorophenol red, nitrazine yellow, bromthymol blue, bromoxylenol blue, neutral red, phenol red, thymol blue, xylenol blue and m-cresol purple or combination thereof. According to yet another embodiment, the indicator agent is nitrazine yellow.

According to yet another embodiment, the at least one ion-balance reagent is a quaternary amine. According to another embodiment, the ion-balance reagent is selected from the group consisting of: di(alkyl)dimethyl ammonium chloride, N-methyl-N,N-bis(alkanoyl oxyethyl)-N-(2-hydroxyethyl) ammonium methylsulfate, vinylbenzyl dimethylcocoammonium chloride, and methyl trioctyl ammonium chloride or combination thereof. According to a preferred embodiment, the quaternary ammonium salt is selected from the group consisting of: tricaprylylmethyl ammonium chloride, tridodecylmethyl ammonium chloride and cetyltimethyl ammonium chloride.

According to yet another embodiment, the stable indication is detectable for at least 72 hours.

According to yet another embodiment, the pathological condition is selected from the group consisting of bacterial vaginosis, the presence of amniotic fluid, dehydration and Candida.

In a non-limiting embodiment, the absorbent material is selected from the group consisting of: swab, gauze, panty shield, hygienic napkin, a diaper and interlabial absorbent structure.

According to certain embodiments, the biological fluid is a vaginal secretion, amniotic fluid or urine. According to yet other embodiments, the indicator system irreversibly changes color for at least 48 hours when contacted by a vaginal secretion associated with vaginosis or amniotic fluid leakage, but preferably reversibly changes color when contacted by urine.

Advantageously, the pre-formed polymer can be a weakly acidic polyelectrolyte polymer. According to yet another embodiment, the polymer is cellulose or cellulose derivative. According to a preferred embodiment, the polymer is selected from the group consisting of: cellulose, sodium carboxymethyl cellulose, ethyl cellulose, nitrocellulose and cellulose acetate.

The wetting agent preferably is selected from the group consisting of: triethylene glycol, ethylene glycol, sorbitol and 2-ethoxy ethanol and the plasticizer is selected from the group consisting of: castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl)adipate, bis-(2-ethylhexyl)sebacate and dibutylphthalate. According to a preferred embodiment, the plasticizer is selected from the group consisting of: diethyl phthalate, dibutylphthalate, bis-(2-butoxyethyl)adipate and bis-(2-ethylhexyl)sebacate.

According to a particular embodiment, the indicator system comprises cellulose acetate as the pre-formed polymer; a plasticizer selected from dibutylphthalate and dioctylphthalate; 2-ethoxy ethanol as the wetting agent; an ion-balance reagent selected from methyl trioctyl-ammonium chloride and tri-dodecylmethyl ammonium chloride; a competitive reagent selected from citric acid and tartaric acid; and nitrazine yellow as the indicator reagent.

According to one embodiment, the indicator system further comprises a solvent. According to another embodiment, the volume ratio between said indicator system and the solvent is about 150:1 to about 150:30. According to yet another embodiment, the solvent is selected from the group consisting of: acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, volatile ethers, tetrahydrofuran, sesame oil and water. According to a preferred embodiment the solvent is selected from the group consisting of: acetone, tetrahydrofuran and volatile ethers.

According to one embodiment, the method further comprising drying the indicator system prior to the viewing step. Advantageously, the method further comprises removing the indicator system from the article prior to the viewing step.

According to an alternative embodiment, the indication of physiological conditions is a color indication. According to some embodiments, the method further comprises:

providing a color-encoding chart comprising a plurality of color codes and a description of medical condition for each color code; and comparing the color of said indication to the color-encoding chart and interpreting thereby determining the medical condition.

According to yet another embodiment, the color-encoding chart specifies the color codes for a medical condition selected from vaginal infections, bacterial vaginosis, parasitic vaginosis, dehydration and amniotic fluids.

According to yet another embodiment, the indicator system reversibly changes color when contacted by urine. According to yet another embodiment, the indicator system comprises two or more indicator mixtures.

According to yet another embodiment, the secretion-monitoring article further comprising mounting means for placing the absorbent body in a position to receive the biological fluid secreted from the person. The absorbent material is preferably selected from the group consisting of: swab, gauze, panty shield, hygienic napkin, a diaper and interlabial absorbent structure.

BRIEF DESCRIPTION OF THE DRAWINGS

The invention is herein described, by way of example only, with reference to the accompanying drawings.

DETAILED DESCRIPTION OF THE PREFERRED EMBODIMENTS

Figure 1A:
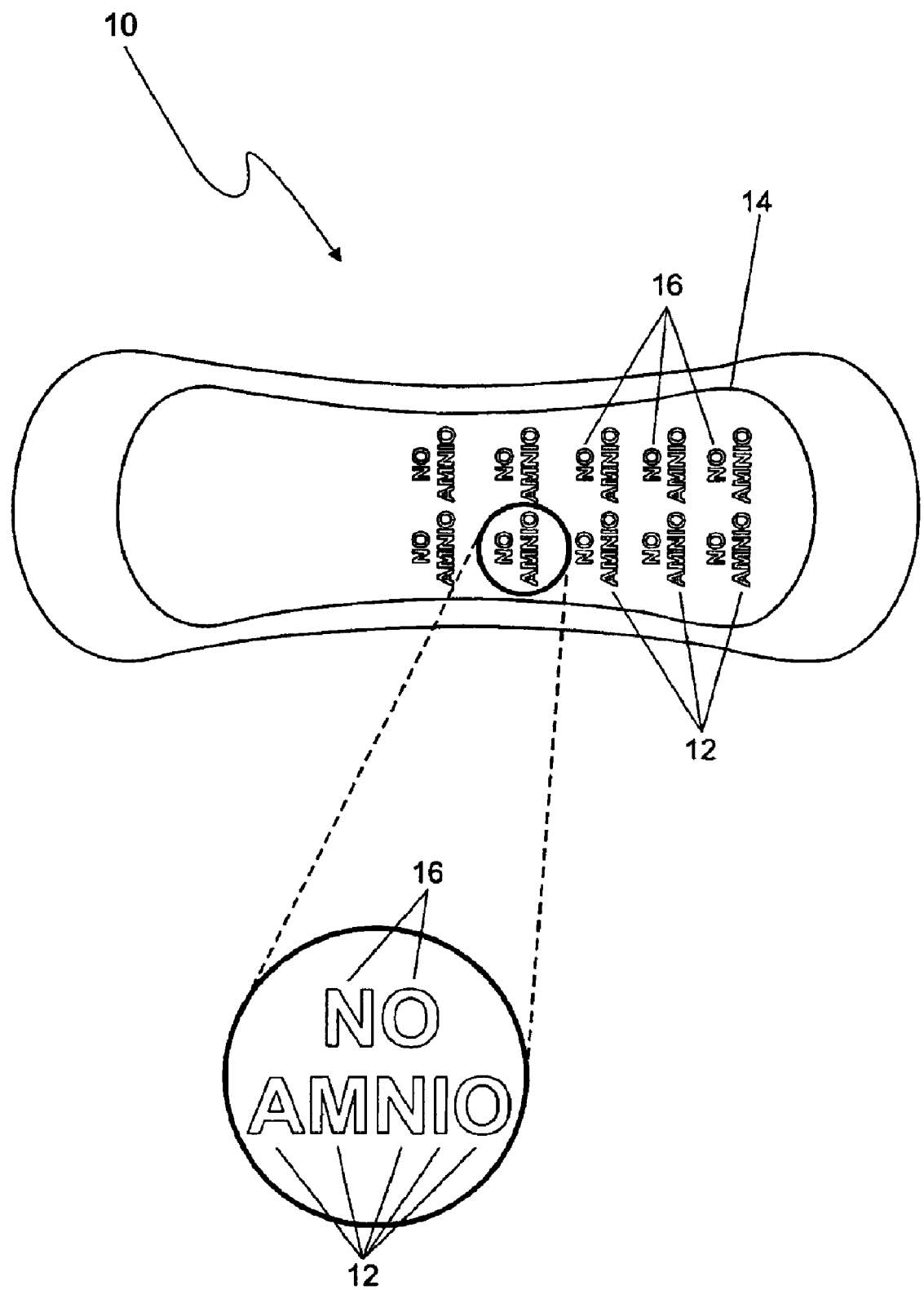
FIGS. 1A-B are schematic top views of an embodiment of the secretion-monitoring article of the present invention with magnification of details of indicators applied to the substrate.

Before turning to details of the present invention, it should be appreciated that the present invention provides a method that allows an untrained user to monitor secreted biological fluids and further allows identifying a pathological condition with confidence. The present invention allows for the identification of a specific pathological condition in biological fluids even when there is a possibility for the presence of an interfering biological fluid with a similar pH. Advantageously, the invention further provides a solution to the common problem of "false positives" associated with diagnostic assays, by providing an indicator composition which comprises at least one indicator reagent and a competitive reagent having a stronger binding affinity to an analyte of interest than the binding affinity at least one indicator reagent to the same analyte. The competitive reagent determines a pre-set threshold of a visible indication, therefore an analyte in a concentration above the pre-set threshold can be readily and accurately detected.

The present invention is an improvement over the prior art, providing a method employing a secretion monitoring article that is more reliable and convenient for the user. The secretion-monitoring article of the present invention comprises an absorbent material for absorbing a biological fluid secreted from a person and an indicator system that has at least one indicator agent that identifies the pH associated with the secretion and an ion balance reagent, the relative amounts of which are unique. Specifically, the amount of the at least one indicator agent does not exceed about 2% and the amount of the at least one ion-balance reagent does not exceed about 5% wherein the percents are weight percent based on the total weight of the indicator system and the total weigh of the mixture equals 100%. The indicator system is associated with an absorbent material such that the biological fluids absorbed by the absorbent material further contact the indicator system so that a reliable indication of the pH of that fluid can be obtained. The indicator system may provide a visible indication of pathological conditions, wherein the visual indication is stable for about a week.

The indicator system utilized by the method of the present invention is capable of providing a visible indication of an analyte of interest in bodily-fluids, the concentration of which is above a predetermined threshold. For this, the indicator system may advantageously comprise a competitive reagent which has the same charge as the at least one indicator reagent. However, the binding affinity of the competitive reagent to the analyte is stronger than the binding affinity of the at least one indicator reagent to said analyte, and wherein the concentration of the competitive reagent determines a pre-set threshold of a visible indication such that upon contact of the composition with a bodily fluid comprising said analyte in a concentration above the pre-set threshold, said composition provides an indication of physiological conditions associated with the pH or the buffer capacities of the bodily fluid.

The terms "stable indication" and "irreversible indication" are interchangeably used herein to describe an indication, typically a color indication, that once obtained remains sufficiently altered for a time sufficient for clinical examination by a professional. Preferably the color change is stable for at least 48 hours, more preferably at least 72 hours, and in some embodiments, preferably the color change is stable for about a week.

The terms "analyte" and "ion of interest" are interchangeably used herein to describe a charged compounds, the presence of which is indicative of a medical condition. According to a particular embodiment, the bodily fluid is vaginal or amniotic fluid and the analyte of interest is a quaternary amine ion.

The term "specific binding", as used herein, refers to binding of two different molecules wherein one of the molecules through chemical or physical means specifically binds to the second molecule, such as binding of an anion to a cation.

The term "tested bodily fluids", as used herein, refers to virtually any bodily liquid sample. The test sample can be derived from any desired source, for example, vaginal secretion, blood, saliva, ocular lens fluid, sweat, urine, milk, ascites fluid, mucous, synovial fluid, peritoneal fluid, amniotic fluid or the like.

The term "indicator reagent", as used herein, refers to a charged binding reagent or a combination of a plurality of charged binding reagents that produce a detectable signal upon contact with a charged analyte of interest. The magnitude and stability of the signal is commonly affected by environmental conditions, particularly, humidity, buffer capacity and pH of the tested bodily fluid. However, due to the unique content of the composition of the invention the indication produced by the indicator reagent is not affected by changes in pH on drying, the presence of interfering biological fluids and repetitive cycles of drying/wetting.

The term "competitive reagent", as used herein, refers to a charged reagent, which is capable of competing with an indicator reagent on the binding of an ion in a tested bodily fluid.

The term "pre-set threshold", as used herein, refers to a specific threshold of ion concentration in a tested bodily fluid, for example ammonium concentration levels in tested urine at values lower or higher than 60 mM; biogenics amines such as diamines, trimethylamine, spermine and tyramine in tested secretion spanning from 0.01 mM to 50 mM; uric acid in tested urine from 0.1 mM to 50 mM, and 0.01 to 80 mM respectively.

The term "substantially different pH ranges" is to be construed in its most general sense and refers to any pH ranges that do not span exactly the same range. Namely, pH ranges having different upper limits and/or different lower limits are substantially different. These different pH ranges may comprise overlapping pH values, such as a pH range of 5.0-8.0 and a pH range of 4.0-7.0 and may be also essentially different, namely, devoid of any overlapping pH values.

The term "about" as used herein refers to +/−10%.

The term "weight percent" as used herein refer to the weight percent of the components of the indicating composition before adding the solvent and before drying, i.e. before reaching the final dry composition. The final dry composition typically does not contain any of the volatile components, namely, water, solvent and the volatile wetting reagent (e.g. 2-Ethoxy ethanol). The volatile components evaporate during the manufacturing process.

The term "normal urine" as used herein refers to urine having normal ammonium concentration and a pH ranging from about 5 to about 8. By contrast, urine of a dehydrated subject has abnormal ammonium concentration, typically, above 60 mM and an increased specific gravity.

Accurate, absolute and fast determination of a medical condition is extremely important in various medical conditions, including, vaginal infections and amniotic leakage. As detailed above, a number of compositions and devices comprising same, having indicators for indicating medical conditions are known in the art. However, they often provide "false positives" due to changes in pH on drying, the presence of interfering biological fluids or due to repetitive drying/wetting cycles. Vaginal infections and amniotic leakage are particular medical conditions that can be diagnosed using the articles known in the art, however, there are often misdiagnosed due to the plurality of substances having similar pH levels, which are commonly present in vaginal secretions. Inaccurate diagnosis of vaginal infections and amniotic leakage due to "false positive" readings is stressful and time consuming to the user.

Amniotic fluid leaking from the vagina of a pregnant woman may occur during pregnancy when the amniotic sac integrity is compromised and a small amount of amniotic fluid may leak out through the cervix and from the vagina. If diagnosed as such, measures such as patient rest or sealing of the amniotic sack using biological glue may be prescribed. If not diagnosed the amniotic sack may later rupture causing abortion of the pregnancy, or require hospitalization of the woman and infant. If the infant is born prematurely, death or severe handicap may be a result. Extended hospitalization of the infant in an incubator is often necessary.

Due to the severe consequences of amniotic fluid leakage, pregnant women undergo severe stress and often go to a health-care professional upon secretion of any liquid from the vicinity of the vagina. The health-care professional looks for the presence of amniotic fluid by checking the pH of the vaginal secretions, amniotic fluid having a pH of between 6.0 and 8.0. Since pregnant women often have urinary incontinence and since urine typically has a pH of between 5.0 and 8.0, if only pH is checked, a false positive result may occur: urine being identified as amniotic fluid. Consequently, it is necessary that such a vaginal secretion be examined using a microscope for the presence of a fern-shaped pattern indicative of amniotic fluid.

As the time between the fluid secretion and the arrival at the health-care professional may be long, there is often no evidence of amniotic fluid upon examination. The secretion may mistakenly be assumed to be urine, often with tragic consequences. On the other hand, the healthcare professional may decide to err on the side of caution, misdiagnosing the secretion of urine as amniotic fluid leading to an unnecessary hospitalization and patient stress.

Commonly, false positive readings of vaginal secretions are caused due to the presence of urine. The pH of vaginal secretions of a patient having bacterial vaginosis is between 4.7 and 6.5. The pH of urine of a healthy patient is within the range of 5.0 and 8.0. Thus, diagnosing bacterial vaginosis with a high degree of confidence cannot be relied upon pH-based test, unless the sample fluid is collected directly from the vagina, where urine is not ordinarily found. However, such examination is uncomfortable and requires intervention of a health-care professional.

The composition of the invention is capable of providing an accurate determination of a medical condition due to its unique content, namely, a pre-formed polymer, at least one indicator reagent being charged oppositely to an analyte of interest in a tested bodily fluid, a competitive reagent having the same charge as the indicator reagent, and at least one ion-balance reagent, wherein the binding affinity of the competitive reagent to the analyte is stronger than the binding affinity of the at least one indicator reagent to said analyte, and wherein the concentration of the competitive reagent determines a pre-set threshold of a visible indication such that upon contact of the composition with a bodily fluid comprising said analyte in a concentration above the pre-set threshold, said composition changes color.

In one embodiment of the invention, the secretion-monitoring article comprises a body that includes an absorbent material for absorbing a biological fluid secreted from a person and an indicator system comprising at least one indicator agent that reacts with biological fluid differently. One example of such an indicator agent is a composition that reacts with fluids containing protonated amine cations, such as urine, in a different way than it reacts to other biological fluids that have a low concentration of protonated amine cations, such as amniotic fluid.

In another embodiment of the invention, the present invention provides a bodily fluid-testing article comprising the compositions of the invention. The article for monitoring of bodily fluids comprises a substrate and an absorbent material for absorbing said bodily fluid, the substrate comprising a composition suitable for identification of a specific ion concentration exceeding a pre-set threshold in a tested bodily fluid, particularly, amniotic, vaginal fluids and urine (for determining dehydration).

The article used for the method of the invention can be embodied as a swab, gauze, shield, hygienic napkin, diaper or interlabial absorbent structure and can be used to indicate the presence of abnormal ammonium concentration in human urine, amniotic fluid leakage, or biogenic secretions associated with bacterial vaginosis, parasite infections, or deficiency of lactobacillus population, without giving a false positive result.

In another embodiment of the invention, the secretion-monitoring article comprises a body that includes an absorbent material for absorbing a biological fluid secreted from a person and an indicator system comprising an indicator mixture that reacts with normal urine differently than infected or protein containing urine. In one non-limiting example, the indicator reacts with normal urine (pH 5-8), which changes the color from yellow to green or turquoise. During the drying process the color change of the indicator that has been contacted with normal urine fades as it dries and becomes yellow again. In contrast, when the indicator is contacted by infected or protein containing urine the indicator strip changes color from yellow to green or turquoise and does not fade when dried. Advantageously, this embodiment is well suited for all types of use, for example in pediatrics, geriatrics, and gynecology, and could be presented to the user in many forms, preferably as a diaper or a panty liner.

According to a currently preferred embodiment of the present invention, an indicating composition is made with nitrazine yellow that indicates the presence of a fluid with a pH of around 4.2 to 7.0. Upon contacting vaginal secretions having a pH of 5.2 or greater, the color changes from pale yellow to blue or green, which indicates possible BV or Trichomonas. At pH of 5.1 or lower, but greater than 4.2, the color change depends on the ionic strength of the vaginal discharge: the more fluidic is the discharge; the change in color is less evident. Fluids with pH levels of 4.2 or lower do not cause a change in the color of the indicating composition.

According to other preferred embodiments, the competitive reagent is an organic acid, the minimal concentration of said organic acid is about 0.25 mM.

The secretion-monitoring article can be implemented using many devices and methods. In a preferred embodiment, the article of the present invention is implemented in a manner that can be easily used by non-skilled personnel, specifically a user. The body of the secretion-monitoring article of the present invention comprising the absorbent material can be supplied to the user, for example, in the form of a pad, gauze, a swab, a fiber ball, but most preferably, as a sanitary napkin, diaper, panty shield, and interlabial structure. Details of manufacture of these are well known to one skilled and have been fully described in the prior art, for example U.S. Pat. Nos. 5,217,444, 5,897,834, and 6,149,590.

Furthermore, any user, male or female, young or old, can use the article in a variety of forms. The particular examples of the invention as presented herein are not intended to limit the scope of the invention, but simply to illustrate and represent the numerous potential forms in which the invention can be used.

Preferably the indication system comprises an indicator mixture as described herein below. As will be discussed in more detail below, more than one indicator systems can be part of the indicator system. The indicator system should be capable of determining substantially different pH ranges, buffer capacities, or capable of reacting differently to different biological fluids to produce a different color change.

In yet another embodiments of the secretion-monitoring article, a means for mounting the article to facilitate the collection of the secreted biological fluid is included. An example of a mounting means that is well known in the art is an adhesive strips associated with the article. In a preferred embodiment the article has one or more adhesive strips. The user removes the release tape to expose the adhesive strip of the article and places the article in the crotch portion of their undergarment. This prevents the article from moving out of position during regular use. Types of adhesive compounds that can be used are well known in the art.

The present invention will be exemplified by embodiments of the secretion-monitoring article of the present invention in the form of a panty shield as presented in FIGS. 1-5. The article can be configured to identify amniotic fluid and secretions associated with bacterial, parasite, fungal, or yeast infection, such as infected urine or vaginal secretions. Furthermore, the article is designed to minimize false positive readings associated with interfering biological fluids.

Figure 1B:
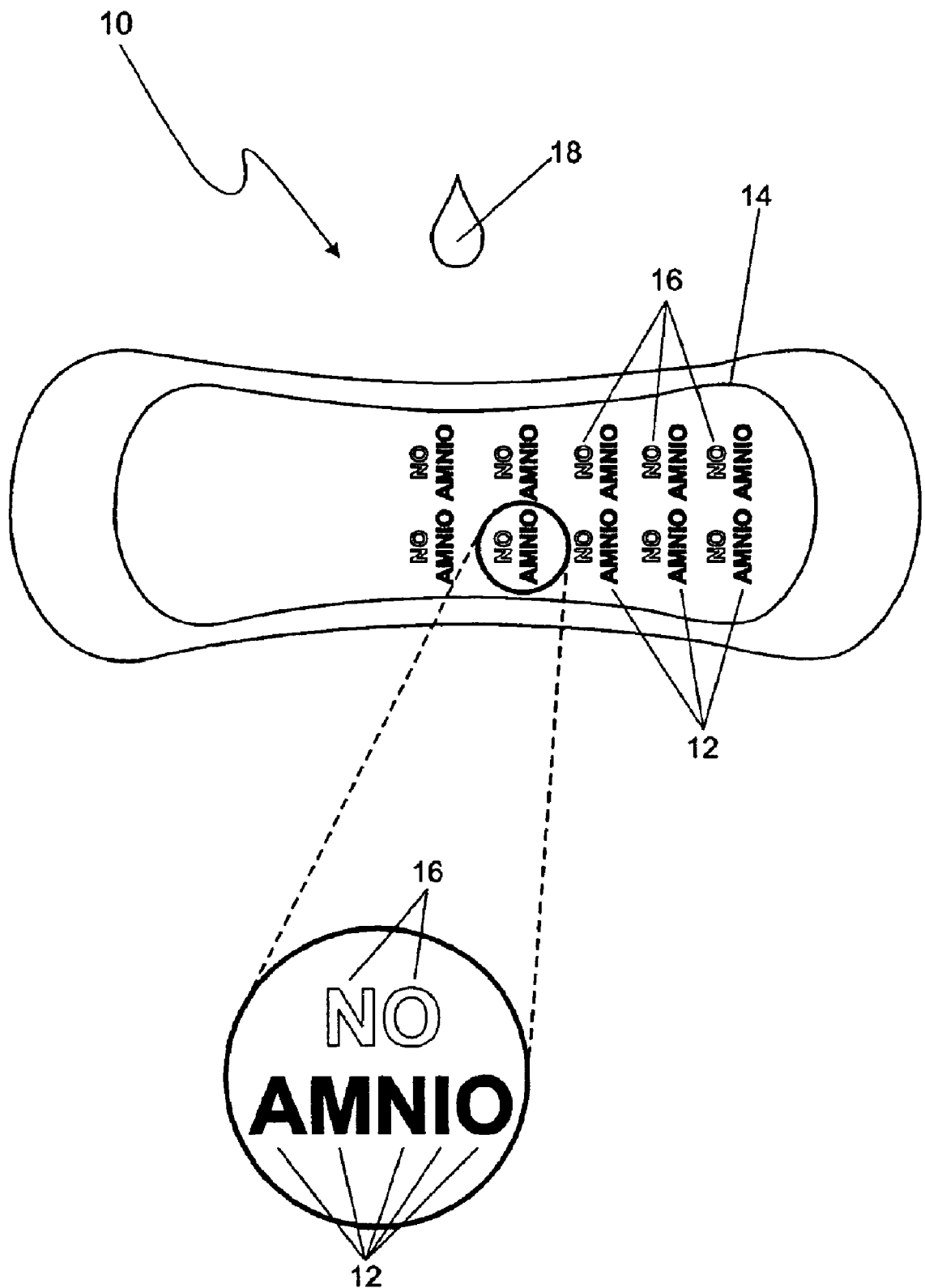
Figure 2:
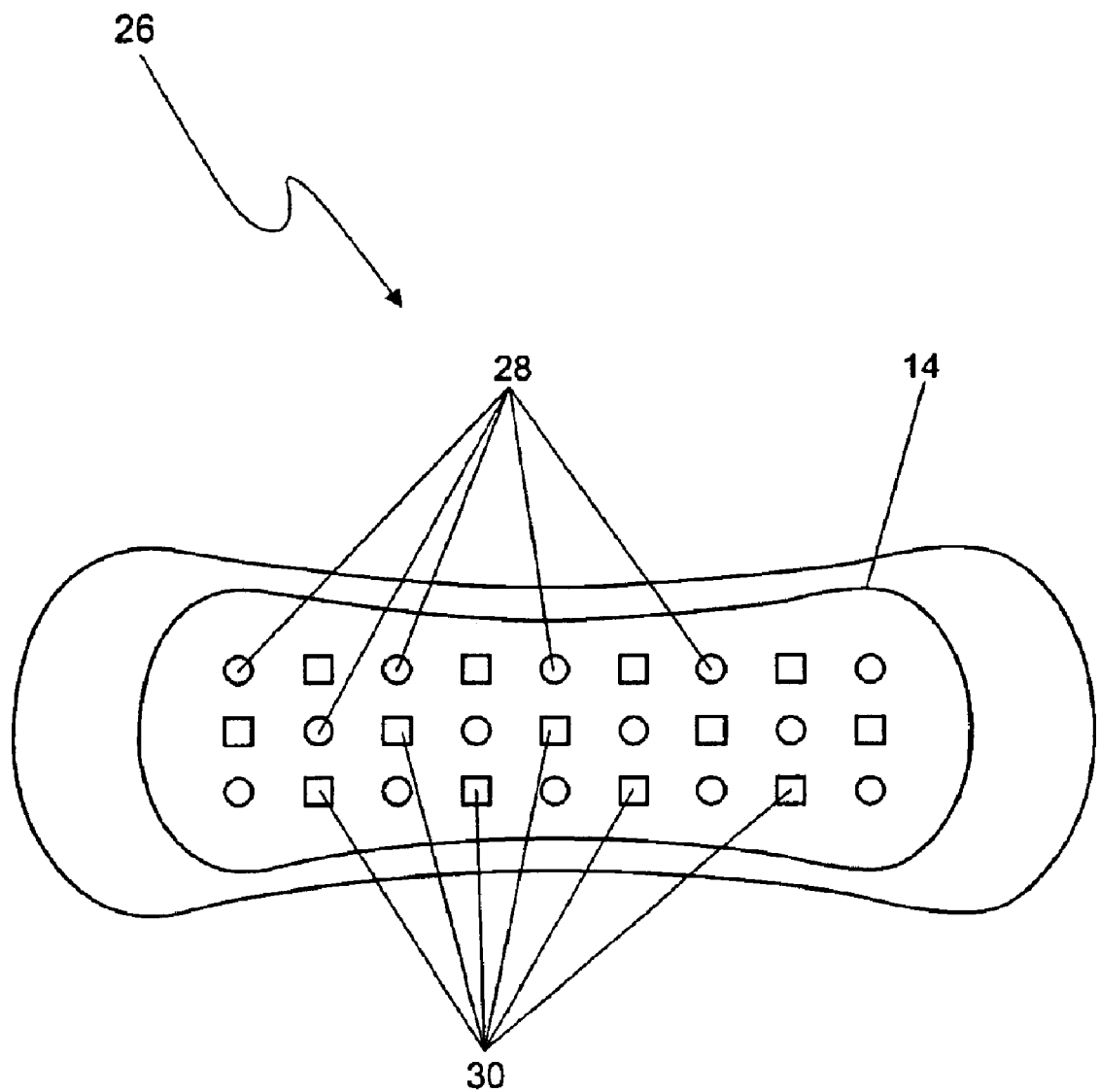
FIG. 2 is a schematic top view of a different embodiment of the secretion-monitoring article of the present invention.
Figure 3:
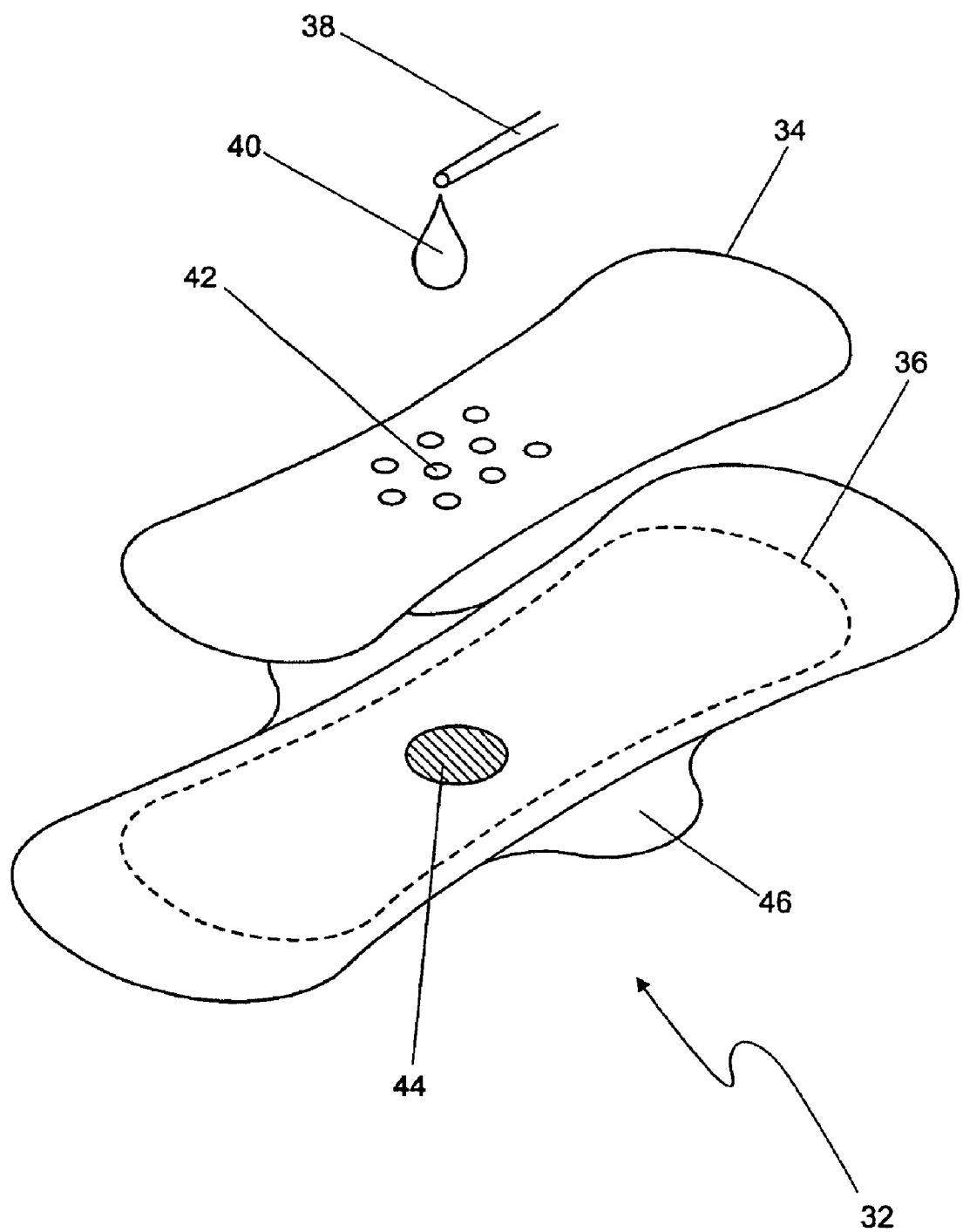
FIG. 3 is a schematic perspective view of a different embodiment of the secretion-monitoring article of the present invention with a microporous membrane.

In some embodiments, the article further comprises a second pH indicator chosen so that it indicates the change of pH as a result of the reaction with a reagent. For example, second indicator in FIGS. 1A-B is m-cresol purple. m-cresol purple is yellow at a pH of below 7.5 and is violet at a pH above 8.0. The second indicator and the reagent are applied at second area 16 on substrate 14, distinct from the first area 12 on substrate 14, FIG. 1A.

In FIG. 1B, amniotic fluid 18 comes in contact with panty shield 10. Amniotic fluid 18 makes contact with first area 12 and second area 16. As the pH of amniotic fluid 18 is between 7.0 and 7.5, the nitrazine yellow present at first area 12 become blue violet, spelling out the word "AMNIO". It is clear to one skilled in the art that if a small amount of fluid is applied to panty shield 20, it is possible that only part of first area 12 will change color. The m-cresol purple present at second area 16 remains yellow.

When the user of panty shield 20 in FIG. 1B examines panty shield 10, she reads the word "AMNIO" and can go to a health-care professional who can take action corresponding to a high degree of certainty of amniotic fluid secretion.

It is clear to one skilled in the art that arranging first area 12 and second area 16 so as to spell out words is not necessary, and in alternative embodiments of the present invention first area 12 and second area 16 may have any shape. For example, in FIG. 2, a panty shield 26 configured in accordance with the present invention is depicted where each one of first area 28 is of substantially circular shape and each one of second area 30 is substantially square shaped.

When used in a medical setting, it is imperative that there be substantially no leaching of indicator system components from the substrate to which the indicator system is attached. The attachment of indicators to a substrate is well within the ability of one skilled in the art. One family of chemical compounds that are suitable for use as the indicators of the present invention without leaching are indicators with negative functional groups. Suitable indicators include nitrazine yellow, thymol blue, bromthymol blue, xylenol blue, bromoxylenol blue, phenol red, m-cresol purple, chlorophenol red, bromcresol purple, alizarin, neutral red, and cresol red, see Table 1. A list of other suitable indicators can be found, for example, in U.S. Pat. No. 5,897,834. It is clear to one skilled in the art that the indicators specifically mentioned herein are just examples and any suitable indicators may be used. Further, there may be instances where the first indicator and/or the second indicator are made up of a combination of individual indicators.

TABLE 1

| Indicator | aqueous pH transition range | color change | CAS |
|---|---|---|---|
| 1. Cresol Red | 7.2-8.8 | yellow to reddish purple | 1733-12-6 |
| 2. Alizarin | 5.5-6.8 | yellow to violet | 72-48-0 |
| 3. Bromcresol Purple | 5.2-6.8 | yellow to purple | 115-40-2 |
| 4. Chlorophenol Red | 5.2-8.8 | yellow to red | 4430-20-0 |
| 5. Nitrazine Yellow | 6.0-7.2 | yellow to bright blue | 5423-07-4 |
| 6. Bromthymol Blue | 6.0-7.6 | yellow to blue | 34722-90-2 |
| 7. Bromoxylenol Blue | 6.0-7.6 | yellow to blue | 40070-59-5 |
| 8. Neutral Red | 6.8-8.0 | red to yellow | 553-24-9 |
| 9. Phenol Red | 6.8-8.2 | yellow to red | 34487-61-1 |
| 10. Thymol Blue | 8.0-9.2 | yellow to blue | 81012-93-3 |
| 11. Xylenol Blue | 8.0-9.6 | yellow to blue | 125-31-5 |
| 12. m-Cresol purple | 7.4-9.0 | yellow to purple | 2303-01-7 |

Another non-limiting embodiment of the indicator system of the present invention is a secretion-monitoring article for the identification of vaginal infections such as bacterial vaginosis (BV) or parasitic. According to the present invention, an indicator system is made with a first indicator agent that indicates the presence of a fluid with a pH of around 4.7 to 7.0. The first indicator agent can be chosen, for example, from one or more of the group including nitrazine yellow, bromthymol blue and bromoxylenol blue. As can be seen in Table 1, these three indicators typically exhibit a bluish color when exposed to a fluid with a pH above 7.0. The second indicator can be chosen, for example, from the group including phenol red, thymol blue, xylenol blue and m-cresol purple. As can be seen in Table 1, upon exposure to a fluid with a pH above 8.0 these four indicators become reddish-purple, red, blue and violet.

As discussed hereinabove, urine of a healthy patient has a pH between 5.0 and 8.0. A patient having BV or parasite also has vaginal secretions with a pH between 4.7 and 6.5. If the liquid examined in the second embodiment of the secretion-monitoring article of the present invention is associated with BV or parasite, the indicator changes color.

EXAMPLES

The following examples set forth preferable embodiments of the present invention.

Example 1

Reducing Erroneous Readings of Color-Changing Devices that Give an Indication of Elevated pH in the Vaginal Secretion The following example discloses the solution to produce an indicator that needs no color-table or scale to read results, that shows the user a stable indication for a few days, and that does not leach even when in contact with liquids for any practical length of time. For the non-invasive continuous monitoring version, the invention discloses a solution to avoid false positive readings due to urine contamination.

The device is a sticker or a pantyliner that contains two different indicator strips, embedded between layers of one-way absorbent tissues. The two indicators have a color transition-point at different pH levels. The color-reactions of the two indicators also have different reversibility in vaginal secretion Vs urine.

The first indicator strip changes color to stable blue, when sensing elevated pH in vaginal secretions (pH strip). The pH strip contains the pH indicator-nitrazine-yellow, which has a pKa of 6.6 in aqueous solution, and with the innovative specific composition, changes the color when the vaginal secretion has a pH level of 5.0 or higher (the same innovative specific composition produces indicators for various pH levels, by using other negatively-charged members of the Ionizable phenol group).

In a case where vaginal secretion with elevated pH (5.0-7.0) will reach the strips only the pH strip will change color and the change will remain stable for a few days.
Method of Preparation (1) pH Strip:
Step 1: To a 10 ml of Acetone add 150 mg Cellulose acetate, 107 μl Dibutylphthalate, 23 μl Aliquat, 150 μl 2-Ethoxy ethanol and 2.4 mg nitrazine yellow dissolved in 150 μl DDW.

Step 2: Stir the mixture for few minutes to complete dissolving.

Step 3: Coat a polyester monofilament screening fabric with the polymer solution (coating other materials un-sensitive to acetone will produce various devices for various using instructions, with the same features).

(2) Urine Strip:
First layer-step 1: To a 4.15 mL DDW add 45 mg PVP, 0.325 mL urease/glycerol solution.

First layer-step 2: Coat a polyester monofilament screening fabric with the polymer solution.

First layer-step 3: The coated strips are dried-out over night at room temperature.

Second layer-step 1: To a 10 ml of THF add 150 mg Cellulose acetate, 107 μl Dibutylphthalate, 23 μl Aliquat, 150 μl 2-Ethoxy ethanol and 1.2 mg m-Cresol purple dissolved in 120 μl 1-Propanol.

Second layer-step 2: Stir the mixture for few minutes to complete dissolving.

Second layer-step 3: Coat the strip with the second polymer solution.

Second layer-step 4: After drying over night the wash the strip in a saline solution.

The device can be in the form of a swab with a tip produced in the same way as mentioned above, under the header: pH strip. The tip may be prepared by using a short strip, rolled on the stick of the swab, or by coating the tip of an integrated swab (implementing step 3), where the tip consists of any screening fabric.

Example 2

A Device Able to Distinguish Accurately Between an Amniotic Fluid Leak or an Elevated pH Vaginal Discharged Secretion and Wetness Caused by Urine Incontinence Due to the severe consequences of amniotic fluid leakage, pregnant women undergo heavy stress and tend to seek for a health care provider upon any wet sensation in the area of the vagina. The common ways to checks for the presence of amniotic fluid are by examining the pH of vaginal secretions with pH indicators such as nitrazine indicators, running the Fern-test or by visually identifying the source of the leakage.

Amniotic fluid has a pH level that varies between 6-8 and can be identified by a purple-blue color of a nitrazine indicator. Since urine, has a pH level that varies between 5.0-8.0, measuring pH levels as a sole criterion can mislead to erroneous decisions. As the other two ways can be performed only in clinics and hospitals, and by trained staff, there is no practical solution for home monitoring.

In some situation, after amniocentesis tests and other occasions such as hi-risk pregnancies, there is a possibility of small amniotic leaks that can be detected only by continuous monitoring.

Current solutions and earlier inventions fail to serve as a home-use continuous monitoring device, as they leach in fluids, the color change is unstable, and the overlap between amniotic fluid pH level and the urine pH level misleads the users in as 30% of the cases.

The overlap of pH levels, between amniotic fluids and urine is also a great disadvantage for physicians treating patients with wet sensations. Providing pregnant women with a home-use continuous monitoring device, that distinguishes amniotic fluid leakage from urine incontinence with no false alarms, enabling the result reading at personal timing and discretion, and detects any small amniotic leak instantaneously, can on one hand help bring the user in-time to hospital when needed, and on the other hand avoid unnecessary hospitalization and concomitant patient stress.

Providing physicians with a reliable clinic instantaneous detecting article, that distinguishes amniotic fluid leakage from urine incontinence with no false alarms, can serve them by far better than available solutions today.

The methods of the present invention are particularly useful for detecting amniotic leakage as they enable to distinguish accurately between normal and abnormal ammonium concentrations in urine, to thereby indicate the hydration level of monitored subject. According to one embodiment, the article of the present invention can be used for the identification of amniotic fluid leaking from the vagina of a pregnant woman. In addition, the article of the present invention is able to detect pH changes above a pre-set threshold specific to amniotic fluid in the vaginal fluids (see Example 12).

According to some embodiments, the compositions of the invention enable to distinguish accurately between ammonium concentrations levels at values lower or higher than 60 mM.

The indicator system of the present invention can be a sticker or a pantyliner with an embedded indicator strip. In a particular example, the strip contains the pH indicator-nitrazine-yellow which has a pKa of 6.6 in aqueous solution.

Reaction of the indicator system of the present invention with amniotic fluid (pH 6-8) changes the color from yellow to stable dark blue. Reaction of the indicator with urine (pH 5-8) changes the color to fading green or fading turquoise. Urine with lower pH 5-5.5 does not change the indicator color.

The difference between the color reaction of the indicator with amniotic fluid and with urine consists of two parameters: the chemical composition of the fluids and the indicator's polymer chemical structure.

The following two equations demonstrates the different reactions:

  Equation 1

  Equation 2

KEY:
$X^-$=Base
$NR_4^+$=Ion balance reagent
$R\text{—}O^-NR_4^+$=phenolate-ion balance reagent The ratio of ion-balance reagent versus indicator in the polymer matrix controls the transition point of the color and the color stability while drying. In the drying process the ion pair phenolate (the active site of the indicator)-ion-balance reagent is stable, which cause a stable performance of the color (equation 1—the relative concentration of the component does not change). In a different case where the concentration of the ion-balance reagent in the polymer is higher, the color of the indicator is getting dark while drying. The color darkening while drying is due to continuance deprotonation of the indicator's phenol by the basic excess of the ion balance reagent (equation 1—while drying the base concentration is getting high and the equilibrium turned to the right). The optimum molar ratio of ion-balance reagent to indicator is 10:1.

Ammonium ions in solution react like the ion-balance reagent and compete with the phenolate active site. While drying the ion pair phenolate-Ammonium hydrolyzed spontaneously to give the protonated yellow phenol (equation 2) while the phenolate-ion-balance reagent pair is stable (equation 1).

In a case where the medium contain ammonium ion the color changes govern by the relative concentration of the ion balance reagent in the polymer and the ammonium ion in the medium.

For example: in 100 mM buffer solution that contains 25 mM ammonium ion the concentration of the ammonium is in two orders of magnitude higher than the ion balance reagent in the polymer. These differences govern the turquoise color in solution and the fading color on drying.

Urine contains ammonium ions in concentration of 30-50 mM; amniotic fluid doesn't contain any substantial amount of ammonium ions, thus causing no fading influence as urine does.

Method of Preparation:
Step 1: To a 10 ml of Acetone add 150 mg Cellulose acetate, 107 μl Dibutylphthalate, 23 μl Aliquat, 150 μl 2-Ethoxy ethanol and 2.4 mg nitrazine yellow dissolved in 150 μl DDW.
Step 2: Stir the mixture for few minutes to complete dissolving.
Step 3: Coat a polyester monofilament screening fabric with the polymer solution to give the desired product.

The device can be a swab with a tip produced in the same way as mentioned above, under the header: pH strip. The tip may be prepared by using a short strip, rolled on the stick of the swab, or by coating the tip of an integrated swab (implementing step 3), where the tip consists of any screening fabric.

Example 3

A Device Able to Distinguish Accurately Between Normal Urine and Infected Urine

The reoccurrence of urinary tract infections in certain patients present the need to quickly and easily diagnose whether the patient has another urinary tract infection. Presently, to determine if a patient has a urinary tract infection they must make an appointment to visit a doctor. Furthermore, if the patient is susceptible to the reoccurrence of urinary tract infections they must make periodic visits to the doctor's office to ensure that the infection has not reoccurred. Having a device that would allow the user to determine if they had a urinary tract infection again would minimize stress and time consumed by visits to the doctors office and result in quicker diagnosis of the infection, resulting in a reduction in pain suffered by the patient and a more timely treatment of the infection.

The article in this example is a diaper or a panty liner with an indicator that can distinguish between normal urine and infected urine. The user wears the article so that urine can come in contact with the article. The reaction of the indicator with urine (pH 5-8) changes the color from yellow to green or turquoise. The drying process of the indicator strip at room temperature is short (5 minutes). When normal urine comes in contact with the indicator strip the color changes fade while drying. The color change is completely reversible and the strip becomes yellow again. On the other hand when infected urine comes in contact with the indicator strip the color changes to green or turquoise and stay constant while drying.

The reversibility of the color changes depends on two different environmental factors:
1. Chemical Environment:
   (a) The pH level of the fluid-pH level higher than the pKa gives a stable color change.
   (b) Buffer capacity of the solution explained extensively in EXAMPLE 4.
   (c) Ammonium salts content in the solution-explained extensively in EXAMPLE 2.
2. Biological Environment:
   (a) Protein presence in urine gives a stable color change and the reaction is not reversible.

Infected urine provides a stable color change to the indicator, which color change is not reversible. Furthermore, bacteria presence in vaginal secretion fluid also gives a stable color change so that the color change is not reversible.

Example 4

A Device Able to Distinguish Between Bacterial or Parasitic Infected Secretions and Normal or Candida Vaginal Secretions. Advantageous Attributes of Polymer Matrix Compared to Commercially Available pH Indicator Paper The buffering capacity of vaginal secretions was studied. In view of these findings the chemical attributes of the polymer matrix of the invention compared to commercially available pH indicator paper were also studied. It was determined that because of the high quantity of homogenous secretions typical of BV, that vaginal secretion associated with BV have a low buffer capacity due to transudation of extracellular fluid.

Bacterial vaginosis (BV) is characterized by production of increased quantities of malodorous vaginal discharge. The vaginal discharge of women with BV is described as being thin (low viscosity), off-white-gray (milk-like consistency), and homogeneous (distinctly not curd-like).

In the vagina there are no glands so that the fluid which it contain results from cervical secretion, vulvar secretions from sebaceous, sweat, Bartholine and Skeens glands, exfoliated cells, endometrial and oviductal fluids but mainly from liquid transudation through the vaginal epithelial walls.

As mentioned above, one of the characteristic of BV is the homogeneous discharge. A women having BV typically has an increase in the discharge amount. The source of this liquid is extracellular fluid (interstitial fluid) that surrounds the epithelial cells in the vagina wall.

The ionic composition of the extracellular fluid and the plasma is quite similar with some differences reflecting the inability of large solutes, like proteins, to cross the cells wall.

A decrease in protein levels and other large organic molecules and the increase of water content in BV secretions lowers the buffering capacity of the secretions. Thus, secretions associated with BV have a lower buffer capacity than healthy vaginal secretions.

Experimental and Results

Polymer Color Change in Solution:

TABLE 2

Color change of polymer mixture dependent on pH

| pH (±0.05) | 100 mM | 50 mM | 20 mM | 10 mM | 5 mM |
|---|---|---|---|---|---|
| 4.0 | 0 | 0 | 0 | 0 | 0 |
| 4.3 | 0 | 0 | 0 | 0 | 1 |
| 4.5 | 0 | 0 | 0 | 1 | 1 |
| 4.7 | 0 | 0 | 1 | 1 | 2 |
| 5.0 | 1 | 1 | 1 | 2 | 2 |
| 5.2 | 1 | 1 | 2 | 2 | 2 |
| 5.5 | 2 | 2 | 3 | 3 | 3 |

*Color scale conversion: 0 - Yellow; 1 - Light Green; 2 - Green; 3 - Dark green;

A follow-up experiment was done using commercially available nitrazine Paper (APOTHECON Inc., Princeton, N.J.) with the same regime of pH buffer solutions. The nitrazine Paper did not significantly change color in any of the pH buffer solutions. The results indicated that the commercially available nitrazine Paper sensitivity was insufficient to indicate a color change significant enough to distinguish and identify the difference in pH of any of the measured solutions.

It is known that nitrazine yellow is a weak acid pH indicator, which when dissolved in water dissociates slightly and form the conjugate base:

$$\underset{\substack{Acid \\ (Yellow)}}{HIn_{(aq)}} + H_2O \rightleftharpoons \underset{\substack{Conjugate\ base \\ (Blue)}}{H_3O^+ + In^-}$$

Figure 6:
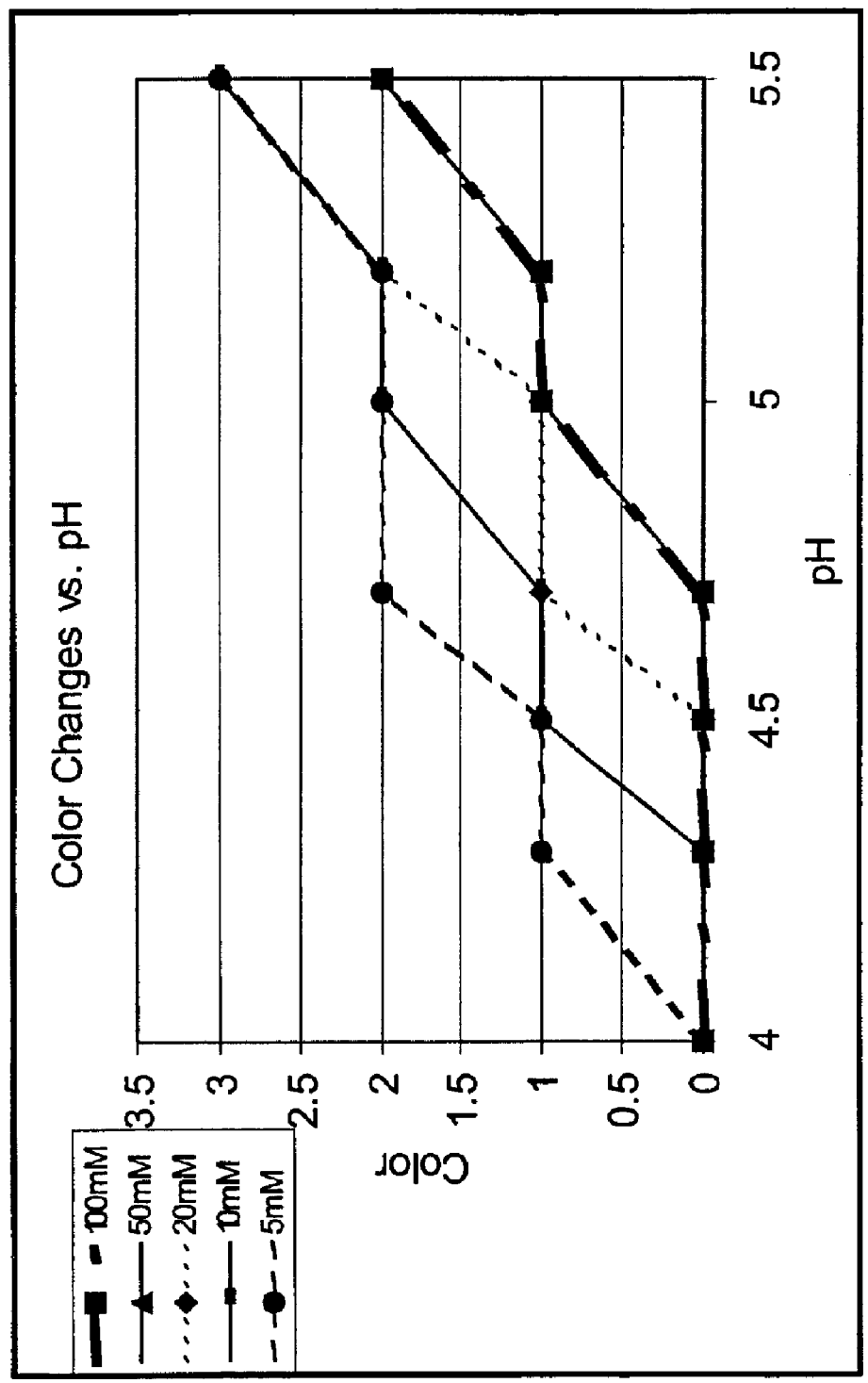
FIG. 6 is a graph showing the change in color of the polymer vs. the change in pH, wherein the color scale conversion is as follows: O-Yellow; 1-Light Green; 2-Green; 3-Dark green.

It is clear from the results (Table 2; FIG. 6) that when the buffer capacity of the solution is lower the color change occurs at a lower pH. The variation between the first color change in the 5 mM buffer solution is approximately 0.7 pH units lower than the first color change of the 50 mM buffer solution.

This is achieved in the polymer matrix of the invention indicator because of its unique formulation. The nitrazine yellow (NY) environment in the polymer matrix is hydrophobic, composed of electronic neutral organic substrate except of the ion balance reagent that does not contribute to the acid-base balance. In contrast, the chemical composition of the commercial nitrazine Paper is a hydrophilic formulation that contains some degree of ionic buffer.

The mechanism of the color changes of the polymer matrix is described in the following equation:

$$\underset{NY\text{-}yellow}{ROH} + \underset{Ion\ balance\ reagent}{NR_4^+} + \underset{Base}{OH^-} \rightleftharpoons \underset{NY\text{-}complex\ blue}{RONR_4} + \underset{water}{H_2O}$$

The reaction is in equilibrium and the color of the polymer depends on the ratio of free NY compared to the NY complex.

In solution the color change is governed by the pH and the buffer capacity. On the drying process of the polymer matrix, the NY complex dissociates easily when the buffering system is highly concentrated or when there is high concentration of protonated cations like $NH_4^+$ in urine. The dissociation of the complex occurs due to the basic nature of the phenolate ion in in the NY complex and the high concentration of protons compare to the Ion balance reagent. The dissociation of the complex express in color changes from green or blue to yellow. On the other hand when the buffer is weak or the medium is highly watery the NY-complex stay stable at any color including the light green one. The stability of the color is due to the lack of protons compared to the Ion balance reagent concentration.

Assessment of Buffer Capacity of Vaginal Secretion:

In order to examine the buffer capacity of vaginal secretions, different buffer solutions were titrated with 0.1 N NaOH in comparison with vaginal secretions.

Figure 7:
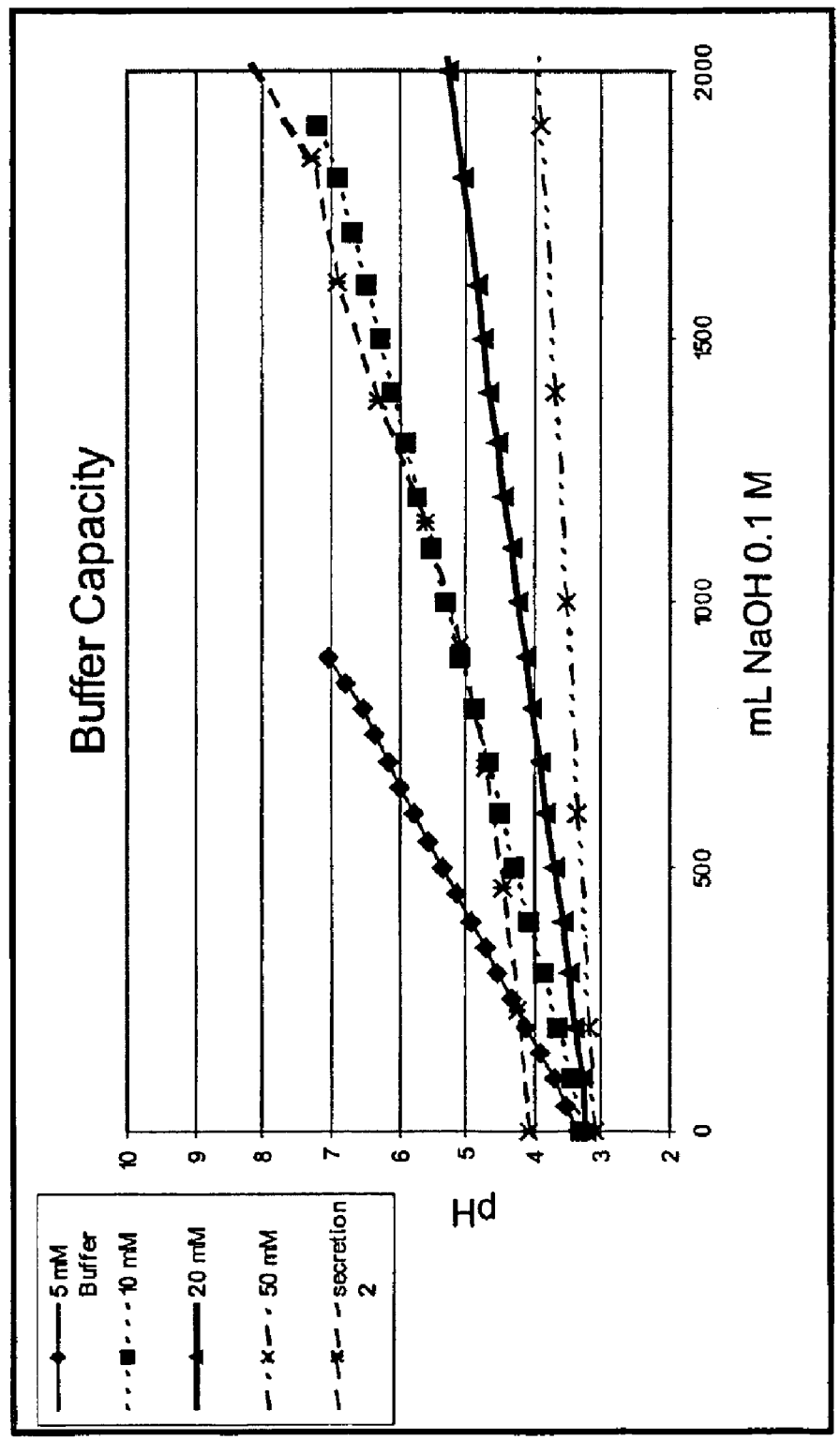
FIG. 7 is a graph demonstrating the buffering capacity of vaginal secretions. The graph compares the pH of the butter or secretion being titrated to the mL NaOH 0.1 M added.

The vaginal secretions were collected with a sterile swab. The sterile swab was weighted on an analytical balance before and after secretion sampling. The secretion was then diluted in double distilled $H_2O$ and titrated as the other buffer solutions with NaOH 0.1M. The dilution factor was taken in account in determining the buffer capacity of the vaginal secretion. The results of the titrations are summarized in FIG. 7.

This study validates that the nature of color changes of the polymer matrix of the invention has an advantage compare to commercial nitrazine paper or devices based on nitrazine paper in detecting infection which has low buffer capacity characteristics. For example infected vaginal secretion with pH levels of 4.3-4.9 and low buffer capacity will be detected by the polymer of the invention while will not be detected by commercial nitrazine paper.

It is standard practice, for patients with vaginal symptoms, to rule-out BV and Trichomonisis and treat for Candida. As the color change caused by vaginal secretions infected with Candia is similar to the color change obtained with normal vaginal secretion, the article of the invention may be used to distinguish vaginal secretions infected with Candia from vaginal secretions infected with BV and Trichomonisis. The article of the invention thus provides a simple test for eliminating BV and Trichomonisis from consideration thereby providing treatment merely for Candida.

Yet another medical condition requiring an accurate determination of specific ion concentration in a tested bodily fluid is dehydration. Dehydration is a condition in which the body or certain body tissues suffer from lack of water and important blood ions like potassium (K+) and sodium (Na+). Vital organs like the kidneys, brain, and heart cannot function without a certain minimum of water and salt. Tissue dehydration may occur in dry climates and during the winter heating season. Extremely dry air causes the rapid evaporation of water from the skin and from the mucous linings of the respiratory system.

Causes of dehydration include excessive fluid losses, inadequate fluid intake, or a combination of these factors. Illnesses that produce diarrhea and vomiting are common causes of dehydration, since both conditions cause loss of body fluids. Other causes of dehydration include diabetes, kidney disease, excessive use of diuretics, liver disease resulting in accumulation of fluid in the abdominal cavity, inflammation of the abdominal cavity resulting in fluid accumulation and burns.

Premature or preterm babies, infants and children are more susceptible to dehydration than adults because of their smaller body weights and higher turnover of water and electrolytes. The elderly and those with illnesses are also at higher risk. In underdeveloped countries, dehydration from diseases like cholera and dysentery kills millions every year (usually infants and children).

For infants, dehydration can develop quickly and even become life threatening if not treated properly. It is therefore very important to recognize the dehydration instantly. The early symptoms of dehydration are urinating smaller amounts than usual and dark yellow urine, since the kidneys retain more water and urine is more concentrated. The color and clarity of urine, the urine specific gravity, and the presence of ketones in the urine may all help to indicate the degree of dehydration. A high urine specific gravity indicates significant dehydration.

Thus, according to one embodiment, the article of the present invention can be used to distinguish accurately between normal and abnormal ammonium concentration in the tested urine (i.e. between normal urine and urine of a dehydrated subject) without any interference of other biological fluids. The article of the present invention is able to detect ammonium cations below or above a pre-set threshold of 60 mM. The present invention provides a monitoring article that uses ammonium ions concentration in the urine as an indicator of the hydration state of the tested subject.

Dehydration is classified as mild, moderate, or severe based on how much of the body's fluid is lost or not replenished, depending on age. Mild dehydration is defined as a loss of 3-5% of body weight; Moderate dehydration is defined as a loss of 6-10% of body weight; and severe dehydration is defined as a loss of more than 9-15% of body weight. When severe, dehydration is a life-threatening emergency.

Improved Methods for Attaching Indicators to a Substrate

Details and variations concerning the method of manufacture of a secretion-monitoring article for implementing the indicator system of the present invention or applying the method of the present invention are well described in the prior art.

As described hereinabove, U.S. Pat. No. 5,897,834 describes a solid pre-formed polymer to which quaternary ammonium groups are covalently bound. Negatively charged indicators are non-covalently bound to the polymer. The non-covalent bonds are strong enough so that the attached indicators do not leach out in an aqueous solution. In addition, the indicators bound to the polymer have a sharpened pH color transition, allowing an accurate determination of the pH of the applied fluid. The polymer can be applied to various substrates. However, indicators bound to these polymers are less useful in non-clinical settings as the indicated pH of vaginal secretions after drying is lower than that of fresh vaginal secretions, leading to false positive results.

In the present invention is disclosed a method suitable for attaching indicators to a substrate so that the indicators do not leach out in an aqueous fluid. Especially suitable indicators are those with a negatively charged group, such as those listed in Table 1 or, for example, in U.S. Pat. No. 5,897,834. The polymer of the present invention is exceptionally suited for attaching the indicator system of the present invention to a substrate. Further, experiments show that unlike other methods and polymers known in the art, changes in color of indicator attached according to the methods of the present invention are fast. The color is retained over a long period of time, as detailed in Example 7, and even when the applied liquid dries. Repeated cycles of drying and wetting also do not change the color. Thus, in practical terms, there is time for a user to get to a health care professional without the color of the indicator changing.

Application of Indicator to a Substrate.

In a first embodiment of the method of the invention for attaching an indicator to a substrate, an indicator is mixed with a preformed polymer in a suitable solution and then applied to a substrate.

In more detail, a polymer solution is prepared containing dry pre-formed polymer, plasticizer, a wetting agent, an ion-balance reagent, a solvent and an indicator. When practicing the method of the present invention, a reagent as described is also added.

The preformed polymer can be selected from various preformed polymers, although cellulose polymers such as nitrocellulose, cellulose acetate or ethyl cellulose are preferred. The preformed polymer makes up 30% to 50% of the weight of the solution. In certain embodiments, the polymer makes up 33% to 45% of the solution. However, in the absence of a wetting agent the preformed polymer may make up about 60% of the weight of the solution. As is clear to one skilled in the art, it is also possible to use a combination of suitable preformed polymers when making one polymer solution.

Although any suitable plasticizer can be used, bis-(2-butoxyethyl) adipate (BBPA, CAS 141-18-4), bis-(2-ethylhexyl)sebacate (DOS, CAS 122-62-3), diethyl phthalate (DEP, CAS 84-66-2) or dibutyl phthalate (DBP, CAS 84-74-2) are preferred. The plasticizer makes up 20% to 30% and 23% to 35% by weight of the composition. In the absence of a wetting agent the plasticizer may make up about 40% of the weight of the solution. As is clear to one skilled in the art, it is also possible to use a combination of suitable plasticizers when making one polymer solution.

Although any suitable wetting agent can be used. In certain embodiments, the wetting agent is volatile and thus most of it evaporates at the final manufacturing step, i.e. drying. According to preferred embodiments, the wetting agent comprises one or more of the following: triethylene glycol, ethylene glycol, sorbitol or 2-ethoxy ethanol are preferred. The wetting agent makes up 20% to 35%, 23% to 34% and 25% to 34% by weight of the solution before adding the solvent and prior to the final manufacturing step (drying). As is clear to one skilled in the art, it is also possible to use a combination of suitable wetting agents when making one polymer solution.

According to further embodiment of the present invention, a competitive reagent can be selected from various competitive reagents such as citric acid, oxalic acid, tartaric acid, succinic acid, glutaric acid, lactic acid, pyruvic acid, hydroxypropionic acid, hydroxyvaleric acid, adipic acid, suberic acid, orotic acid, phthalic acid, 2-[(2-hydroxy-1,1-bis(hydroxymethyl)ethyl)amino]ethanesulfonic acid and 4-(2-hydroxyethyl)piperazine-1-ethanesulfonic acid, although citric acid and tartaric acid are currently preferred.

The competitive reagent makes up 0.2% to 8% and 0.4% to 5% by weight of the composition.

Although any suitable ion-balance reagent can be used, tricaprylylmethyl ammonium chloride (Aliquat 336; CAS 5137-55-3), tridodecylmethyl ammonium chloride (TD-MAC; CAS 7173-54-8) or cetyltimethyl ammonium chloride (CTAC; CAS 112-02-7) are preferred. The ion-balance reagent makes up 1% to 6%, 2% to 5% and 2.5% to 5% by weight of the solution. As is clear to one skilled in the art, it is also possible to use a combination of suitable ion-balance reagents when making one polymer solution.

The components of the solution are added so that the sum of weights of the components prior to the drying step of the manufacturing process is equal to 100%. The components include at least the pre-formed polymer, plasticizer, indicator and ion-balance reagent. In some embodiments the components of the indicator system further include one or more of wetting agent and competitive agent.

The desired indicator is added to the solution. Although any suitable indicator can be used, it is preferred that the indicator molecules have a negatively charged functional group such as acetate or sulfonate. Most preferably, the indicators used, separately or in combination, are chosen from amongst indicators listed in Table 1 and in U.S. Pat. No. 5,897,834. The total amount of indicator added is 0.05% to 2%, 0.05% to 1% and 0.2% to 0.7% of the weight of the polymer solution.

Further, an amount of solvent is added that is suitable for making any easily applied solution/indicator mixture. Typically, 150 mg of polymer solution is dissolved in between 1 ml and 30 ml of solvent or 5 ml and 15 ml solvent. Although any suitable solvent or mixture of solvents may be used, preferred are ethyl acetate or substantially volatile ethers such as diethyl ether, isopropyl ether, t-butyl methyl methyl ether or tetrahydrofuran.

Once the mixture is ready, it is applied by suitable means to the substrate. Application can be done, for example, by spraying or spreading the mixture on the substrate, or by dipping the substrate in the mixture. The substrate can be of many suitable woven or non-woven materials known in the art such as polyester membranes, polypropylene membranes, cellulose membranes, paper, cotton or linen. The structure of the substrate may be, for example, a fiber, a mesh, gauze, a fabric or a membrane. The solvent of the mixture is allowed to evaporate. Once the mixture dries onto the substrate, the substrate is integrated into whatever secretion-monitoring article is desired, such as a panty shield.

As is clear to one skilled in the art that when the indicator system of the present invention is implemented, a first mixture with a first indicator is made, and a second mixture with a second indicator and a reagent is made, both mixtures as described hereinabove. Each of the two mixtures is applied to a predefined area on the substrate, as described hereinabove. Preferably the area of application of the first mixture is substantially distinct from the area of application of the second mixture.

In certain applications, the liquid to be tested may contain biological polymers such as proteins or fats. For example, amniotic fluid and urine often contain proteins. The biological polymers may plug up the pores in the substrate reducing the effectiveness of the testing method. This can be exceptionally significant in panty shield applications such as panty shield 32 depicted in FIG. 3. In such cases, it is preferable to interpose a microporous membrane 34, such as a dialysis membrane (e.g., cellulose membrane, catalog no. D-9402, Sigma-Aldrich, St. Louis Mo.), between indicator substrate 36 and a source 38 of secretion 40). Large-sized materials 42 in secretion 40 cannot penetrate microporous membrane 34 whereas fluid component 44 of secretion 40 penetrates microporous membrane 34 to react with indicator substrate 36. Panty shield 32 in FIG. 3 further includes two side flaps 46 (only one is visible in FIG. 3) configured to allow attachment of panty shield 32 to an undergarment of a user, in such a way keeping panty shield 32 in the proximity of the vagina of a user.

In a second embodiment of the method of attaching an indicator to a substrate according to the present invention, a substrate is first treated with a surfactant solution. After the solution dries, an indicator solution is applied to the substrate. The substrate can then be integrated into a product.

Although any surfactant can be used, when it is desired to attach negatively charged indicators to a neutral substrate, a surfactant with a cationic functional group is used, preferably Aliquat 336, TDMAC or CTAC. Although any suitable solvent or mixture of solvents may be used, preferred are ethyl acetate or substantially volatile ethers such as diethyl ether, isopropyl ether, t-butyl methyl ether or tetrahydrofuran. The surfactant is dissolved in the solvent at any suitable concentration. Preferred is that the surfactant makes up 0.01% to 2% of the solution, more preferred is that the surfactant makes up 0.1% to 0.5% of the solution, and most preferred is that the surfactant makes up 0.15% to 0.25% by weight of the solution.

As is clear to one skilled in the art, it is also possible to use a combination of suitable surfactants. The surfactant solution is applied to the substrate. Application is done, for example, by spraying or spreading the mixture on the substrate, or by dipping the substrate in the mixture. The substrate can be of many suitable materials known in the art such as polyester membranes, polypropylene membranes, cellulose membranes, paper, cotton or linen. The structure of the substrate may be, for example, a fiber, a mesh, gauze, a fabric or a membrane. The solvent of the surfactant solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

After the solvent of the surfactant solution has evaporated, an indicator solution is applied to the substrate. Although any solvent or mixture of solvents may be used, preferred are ethyl acetate or substantially volatile ethers such as diethyl ether, isopropyl ether, t-butyl methyl ether, or tetrahydrofuran. Although any suitable indicator can be used, it is preferred that the indicator molecules have a negatively charged functional group such as acetate or sulfonate when the surfactant used is a cationic surfactant. Most preferably, the indicators used, separately or in combination are chosen from amongst those listed in Table 1 or, for example, in U.S. Pat. No. 5,897,834.

When it is desired to add a reagent in preparation of the indicator system of the present invention, reagent is added to the indicator solution. For example, when urease is used, any suitable amount of urease can be added. Although any suitable concentration of urease can be used, preferred is a concentration of between 1 and 100 unit/ml. More preferred is a concentration of 2 and 50 unit/ml and even more preferred a concentration of 5 and 20 unit/ml.

In an additional embodiment of the present invention, a reagent solution is prepared separately from the indicator solution. When urease is used as a reagent, any suitable concentration of urease can be used. It is preferred that a concentration of between 1 and 100 unit/ml urease be used, more preferred is a concentration of 2 and 50 unit/ml and even more preferred a concentration of 5 and 20 unit/ml.

The indicator solution (or indicator/reagent solution) is applied to the substrate. Application can be done, for example, by spraying or spreading the indicator solution on the substrate, or by dipping the substrate in the indicator solution. The solvent of the indicator solution is allowed to evaporate. Although the solvent may be allowed to evaporate at ambient pressure, it is preferable to evaporate the solvent under vacuum, preferably at a pressure of less than 600 mm Hg, more preferably less than 200 mm Hg, and even more preferably less than 100 mm Hg.

100 mM buffer phosphate citrate was prepared with seven different pH values. Each buffer was diluted to four different concentrations: 50, 20, 10 and 5 mM and the pH was adjusted using NaOH 1M or HCl 1M. A nitrazine polymer matrix of the invention was dipped in each buffer and the change in color was noted and represented by a numeric values as follows: 0=Yellow; 1=Light Green; 2=Green; 3=Dark green. The results are summarized in Table 2 and FIG. 6.

When a reagent solution is prepared separately from the indicator solution, the reagent solution is applied in substantially the same way as described hereinabove, either before or after application of the indicator solution.

Irrespective of the exact concentration of the indicator solution and of the surfactant solution used, it is preferable to apply an amount of each one of the solutions so that the molar concentration of surfactant applied per unit area of substrate is roughly one hundred times greater than the molar concentration of indicator applied per unit area of substrate. The indicator solution is applied to the substrate to areas where surfactant was previously applied.

As is clear to one skilled in the art, when the indicator system of the present invention is implemented, a first solution with a first indicator is made, and a second solution with a second indicator and a reagent is made, both solutions as described hereinabove. Each of the two solutions is applied in distinct areas on the substrate, as described hereinabove.

Example 5

Stability of Indication I

Solution A: 370 mg cellulose acetate, 280 mg DBP, 150 mg sorbitol, 150 mg 2-ethoxyethanol, 50 mg TDMAC were combined. 3 mg Bromthymol blue were added, 20 ml THF were added. The solution was vigorously stirred.

Solution B: 370 mg cellulose acetate, 280 mg BBPA, 300 mg ethylene glycol, 50 mg TDMAC were combined. 3 mg m-cresol purple and 30 units urease were added. 20 ml 20 THF were added. The solution was vigorously stirred.

Solution C: 10 mM buffer Citrate Phosphate solution at different pH values ranging from 3.0 to 7.0. The 10 mM buffer solution was obtained by diluting 100 mM buffer solution. The different pH levels are result of mixtures at different ratios between the buffer components (100 mM Citric acid and 200 mM dibasic Sodium Phosphate) adjusted to the final pH values with 1M Hydrochloric Acid or 1M Sodium Hydroxide solutions.

Solution D: 0.1% BSA in double distilled water and pH 4.5 adjusted to the final pH values with 1M Hydrochloric Acid or 1M Sodium Hydroxide solutions.

(1a) Cotton gauze was dipped in Solution A. When the solution dried, the cotton gauze was cut in half. The first half was dipped in a pH 7 test solution. The first half became purple. The first half was allowed to dry in ambient conditions, with no substantial change of color. After three hours, the second half was dipped in a pH 7 test solution. The second half became purple. The colors of the first half and of the second half were substantially the same.

(1b) Cotton gauze was dipped in Solution B. When the solution dried, the cotton gauze was cut in half. The first half was dipped in urine. The first half became violet. The first half was allowed to dry in ambient conditions, with no substantial change of color. After three hours, the second half was dipped in urine. The second half became violet. The colors of the first half and of the second half were substantially the same.

(1c) Solution A and Solution B were applied in alternating stripes on cotton gauze at a density of about 50 μl/mm². Amniotic fluid was applied to the gauze, changing the color of the stripes of Solution A to purple. Urine was applied to the gauze, changing the color of the stripes of Solution B to violet. The gauze was allowed to dry at ambient conditions for three hours and cut in half Urine was applied to the first half. The colors of the stripes in the first half and the second half of the gauze were substantially the same.

(1d) Strips coated with solutions A or B were dipped in Solutions C and D of various pH values. A color change was observed in all strips. The intensity of the color of strips dipped in Solution C was slightly reduced after 15 minutes of drying however the color maintained for at least 72 hours. The intensity of the color of strips dipped in Solution D was did not change after drying and for the next 72 hours.

Stability of Indication II.

Product Preparation:

To a 10 ml of Acetone the following ingredients were added: 210 mg Cellulose acetate, 107 μl Dibutylphthalate, 32 μl Aliquat, 210 μl 2-Ethoxy ethanol and 3.2 mg nitrazine yellow dissolved in 210 μl DDW. All ingredients were dissolved by stirring the mixture for a few minutes. A polyester monofilament screening fabric was then coated with the polymer solution to give the desired product.

The stability of indication provided by the product of the invention was compared with the stability of indication provided by the following commercial pH indicating articles: nitrazine Paper (Apothecon) and Merck's pH-Indicator strips for pH ranges of 4.0-7.0. The color changes were compared to a reference PANTONE color guide catalogue and the results are summarized in Table 3. The test solutions which were used in this study consisted of 0.1% BSA in water (double distilled) at pH 5.5. The pH was adjusted with solutions of 1M Hydrochloric Acid or 1M Sodium Hydroxide solutions.

TABLE 3

Stability of Indication

| Time | Indicator solution | nitrazine Paper (Apothecon) | pH Indicator Strip (Merck) |
|---|---|---|---|
| 0 | 120 | 131 | 457 |
| 5 minutes | 577 | 1245 | 457 |
| 1 hour | 578 | 117* | 456 |
| 2 hours | 578 | 110* | 456 |
| 24 hours | 578 | 110* | 4515* |
| 48 hours | 578 | 110* | 4515* |
| 72 hours | 578 | 110* | 4515* |

*indicating incorrect pH values in comparison to manufacturer color scale.

Example 6

Articles for Detecting Amniotic Fluids

Three solutions were prepared:
Solution A: 0.2% Aliquot 336 in DDW (double distilled water);
Solution B: 10 unit/ml urease and 0.003% m-cresol purple in DDW; and
Solution C, 0.003% nitrazine yellow in isopropyl ether.

A nitrocellulose membrane was dipped in Solution A and transferred to an atmosphere of 50 mm Hg. After 30 minutes, the membrane was removed from the vacuum. Solution B was applied in a pattern resembling the word "NO" at a density of 50 µl/mm². Solution C was applied in a pattern resembling the word "AMNIO" at a density of 50 µl/mm². The membrane was transferred to an atmosphere of 50 mm Hg. After 30 minutes, the membrane was removed from the vacuum. The membrane was dipped in a pH 7 test solution. The word AMNIO appeared in purple. After drying at ambient conditions for three hours, no substantial change of color was observed. The membrane was dipped in urine. The word NO appeared in violet.

Method of Constructing the Article

Figure 4A:
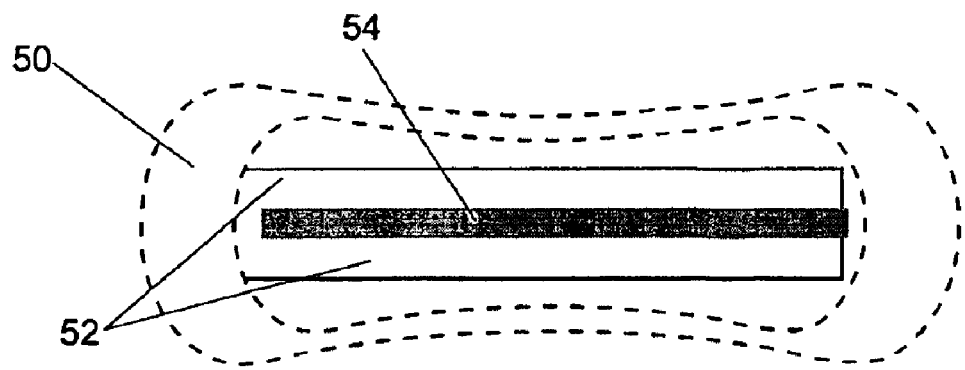
FIG. 4A-C are schematic top views of an embodiment of the secretion-monitoring article with two pH indicators.
Figure 4B:
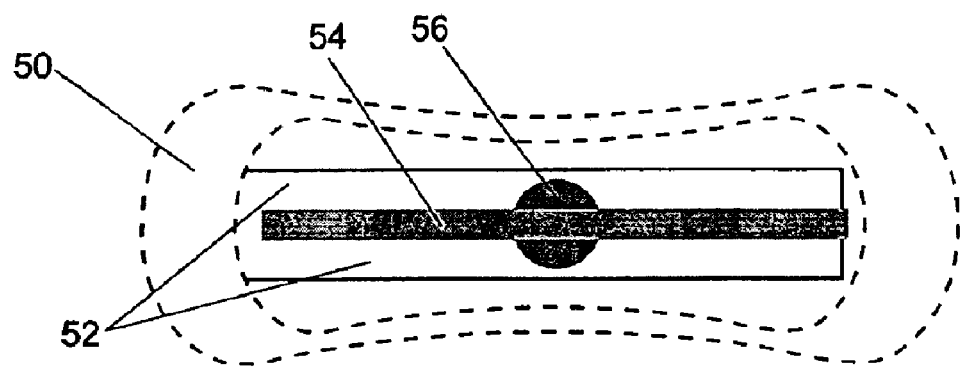
Figure 4C:
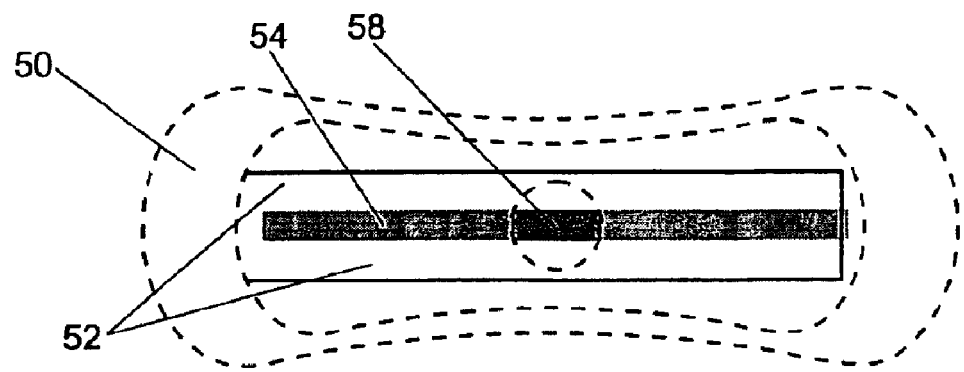

FIGS. 4A-C and 5A-B provide visual examples of two methods non-limiting examples of constructing the article. FIGS. 4A-C show an article in the form of a panty shield 50 constructed with two indicators 52 and 54. In FIG. 4A, the panty shield 50 is constructed with a pH indicator 52 for detecting normal biological fluids and a second pH indicator with high pH dye and a reagent, such as urease, for detecting interfering biological fluids, such as urine. FIG. 4B depicts the panty shield 50 wherein a normal fluid, without an interfering fluid, changes the color 56 of the pH indicator 52. In contrast, FIG. 4C depicts the panty shield 50, wherein an interfering biological fluid, such as urine, changes the color 58 of the second pH indicator 54.

Figure 5A:
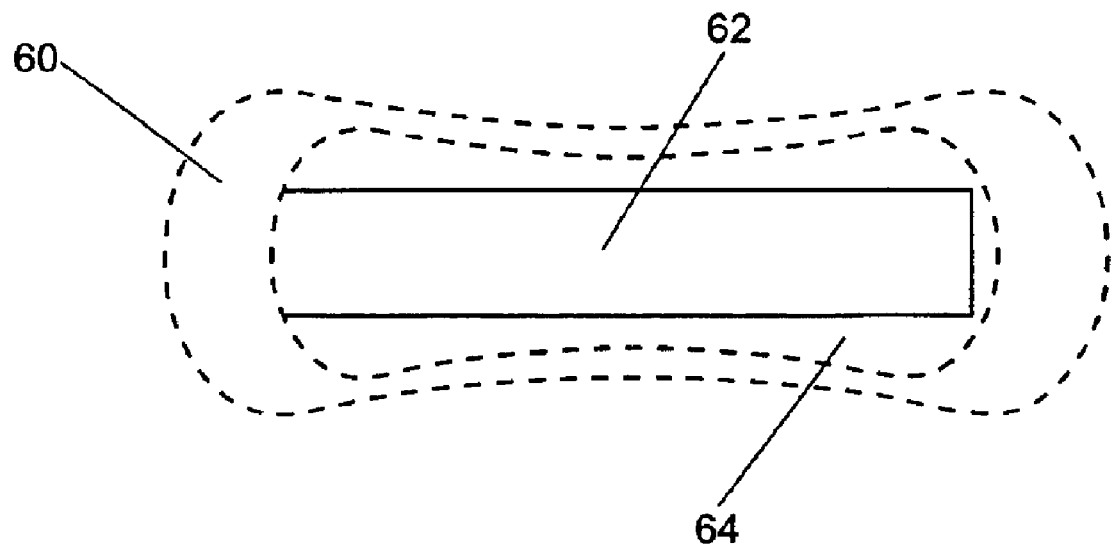
FIGS. 5A-B are schematic top views of an embodiment of the secretion-monitoring article with one pH indicator device that can distinguish between urine and other body fluids, such as amniotic fluid.
Figure 5B:
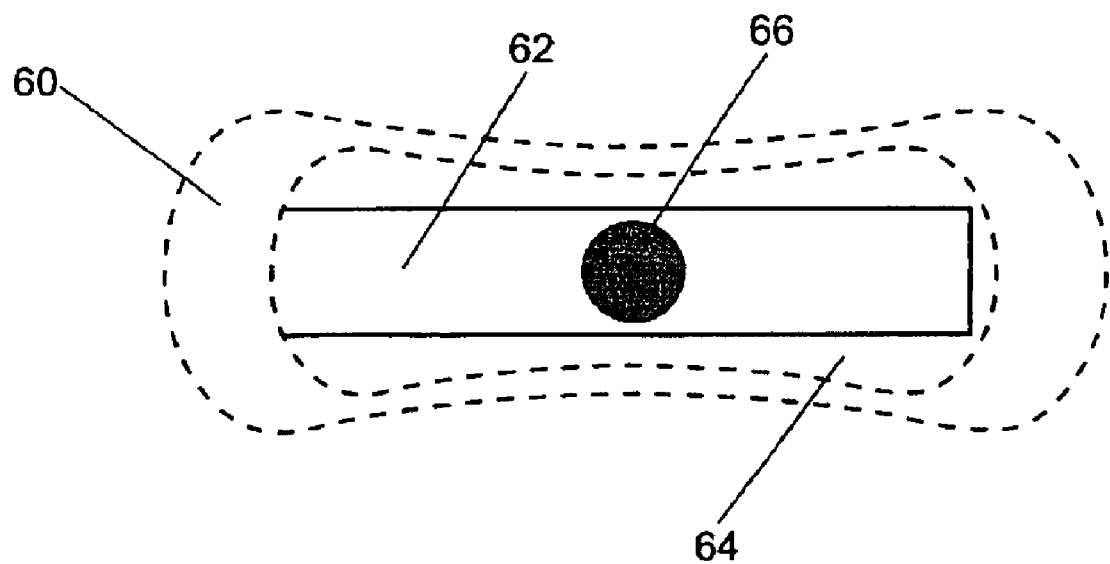

In a separate embodiment, the article can be made with only a single indicator as shown in FIGS. 5A and 5B. FIG. 5A depicts the article in the form of a panty shield 60, comprising a sticker 64, with an indicator 62 constructed so as not to react with an interfering biological fluid like urine. When a biological fluid to be detected comes in contact with the indicator, as show in FIG. 5B, the indicator changes color 66, whereas if the indicator comes in contact with urine it will not change colors.

Example 7

Use of the Articles for Identifying Bacterial Vaginosis

An article, according to any one of the foregoing embodiment, is attached to the underwear of the user such that the indicator strip faces the vagina. Prior to contacting vaginal fluids the color of the indicating composition is pale yellow. Following accumulation of vaginal secretion on the indicator strip, the user removes the article from her underwear and removes the indicator strip from the article. The indicator strip is left to dry for several minutes. For this purpose, the indicator strip may be left to dry at room temperature for about 2 to about 10 minutes. The user than views the color of the indicating strip and interprets the results in accordance with the following color-coding description:

Blue-green color—indicates possible BV (Bacterial Vaginosis) or Trichomonas. Upon appearance of blue color the patient should consult a physician. If the change in color is caused by urine and not by BV than the blue-green color fades away within less than 10 minutes.

Yellow color—indicates low probability of BV or Trichomonas. In such cases, the cause of the vaginal secretion may be yeast or transient irritation.

Upon contacting vaginal secretions having a pH of 5.2 or greater, the color changes from pale yellow to blue or green. At pH of 5.1 or lower, but greater than 4.2, the color change depends on the ionic strength of the vaginal discharge: the more fluidic is the discharge, the change in color is less evident. Fluids with pH levels of 4.2 or lower do not cause a change in the color of the indicating strip.

In the event that the indicator strip stains blue or green, the discharge acidity parameters are disordered and the risk of bacterial or parasitic infection is high; if the indicator strip does not change color or is initially stained blue or green but the color fades back to yellow during the 10 minute drying period, then there is a low probability of bacterial or parasitic infections and a high probability that the discharge was in fact urine.

Example 8

Use of the Articles for Identifying Leakage of Amniotic Fluids

An article, according to any one of the foregoing embodiment, is attached to the underwear of the pregnant woman such that the indicator strip faces the vagina. Prior to contacting any fluids the color of the indicating composition is pale yellow. Following wetness sensation and accumulation of fluid on the indicator strip, the pregnant woman removes the article from her underwear and removes the indicator strip from the article. The indicator strip is left to dry for several minutes. For this purpose, the indicator strip may be left to dry at room temperature for about 2 to about 30 minutes. The pregnant woman than views the color of the indicating strip and interprets the results in accordance with the following color-coding description:

Blue-green color—indicates that the pregnant woman may be leaking amniotic fluid. Upon appearance of the blue-green color the patient should contact her healthcare provider without delay. If the change in color is caused by urine and not by amniotic fluid, than the blue-green stain fades away within less than 30 minutes.

Yellow color—indicates that the wetness was probably not caused by amniotic fluid. In such cases, the cause of the wetness sensation was probably urine.

Amniotic fluid normally has pH levels varying between 6.5 and 7.5 units. Urine has pH levels between 5.0 and 8.0 units. Upon contacting fluids having a pH of 5.2 or greater, the color changes from pale yellow to blue-green. Stains observed on the strip can be caused by either amniotic fluid leak or by urine. After drying up to 30 minutes, stains caused by urine fade back to yellow, while stains caused by amniotic fluid remain stable.

Example 9

Reducing Erroneous Readings of Color-Changing Articles by Using a Charged Competitor Using a negatively charged competitor, such as an organic acid, having a greater binding affinity to interfering cations in a tested bodily fluid than the affinity of a negatively charged indicator reagent, such as nitrazine yellow, results in an accurate indication of the presence of an ion of interest in the tested bodily fluid and enables to avoid false positive readings due to urine contamination.

An indicator reagent produces a color or induces a color change, when the amount of bonded cations per surface is large enough. The end point of the reaction between the tested bodily fluid and the indicator reagent is monitored by the concentration of the competing organic acid, which should preferentially bind to the free cations. The following two equations demonstrate the competitive reactions.

$$RCOOH + NH_4^+OH^- \longrightarrow RCOONH_4 + OH^- + H^+$$

$$InH + X^- + Y^+ \longrightarrow InY + X^- + H^+$$

KEY:
RCOOH=organic acid
InH=indicator reagent
X⁻=OH⁻
Y⁺=quaternary amines
If [RCOOH]≧[Y⁺] no color change will take place. If [RCOOH]<[Y⁺] a color change will occur.

Example 10

Detection of the Concentration of Ammonium Ions in Urine Exceeding a Pre-Set Threshold for Determining the State of Dehydration An indicator reagent shows a color change, when the amount of bonded ammonium cations per surface is above a pre-set threshold. The end point of the reaction between the tested urine and the indicator reagent is determined by the amount of ammonium cations per surface left after the reaction is completed, including a dry-out phase. The threshold of the indication of the ammonium concentration is controlled by the ratio between the organic acid (competitive agent) and indicator concentrations. As the organic acid concentration is increased the sampled urine needs a greater concentration of ammonium cations, to fully cause an irreversible color change of the indicator system. Observation of a visible stable color at the end of the reaction indicates that the ammonium concentration is greater than the pre-set threshold. The following two equations demonstrate the competitive reactions:

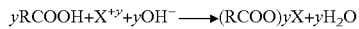

$y\text{RCOOH} + X^{+y} + y\text{OH}^- \longrightarrow (\text{RCOO})_y X + y H_2 O$

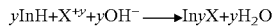

$y\text{InH} + X^{+y} + y\text{OH}^- \longrightarrow \text{In}_y X + y H_2 O$

KEY:
RCOOH=Organic Acid
InH=Indicator reagent
$X^{+y}$=cation, e.g. $Na^+$, $K^+$, $Mg^{+2}$ and $Ca^{+2}$
y=positive charge Thus, this method is based on sensitivity specific gravity. Using such method which is sensitive to the total concentration of all cations in the urine allows detecting an increase in the specific gravity of the urine by its sensitivity to total cations concentration (e.g. ammonium and sodium and potassium etc.) in the urine. Normal values of specific gravity of are between 1.002 to about 1.028. The color change in the indicator system of the invention is observed when the system is exposed to urine simulant with concentration lower than 0.56N X⁺, corresponding to specific gravity of 1.03 which is considered high and implies dehydration state (Table 4). It is noted that the color of the indicator in the dry state of the polymer is the color of its protonated state which is the same color when the specific gravity is high. When cations concentration decreases, the specific gravity decreases also and the sensitivity of the indicator to changes in view the pH—increases.

In the following specific, non-limiting, example, $X^{+y}$ is $NH_4^+$ (y=1):

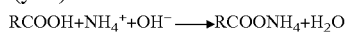

$\text{RCOOH} + NH_4^+ + OH^- \longrightarrow \text{RCOONH}_4 + H_2O$

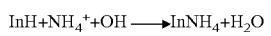

$\text{InH} + NH_4^+ + OH^- \longrightarrow \text{InNH}_4 + H_2O$

KEY:
RCOOH=organic acid
InH=indicator reagent
$NH_4^+$=ammonium cation

Another parameter that can affect the color change of the indicator system upon contacting urine of a dehydrated subject is the ammonium cation concentration. Typically, urine with lower pH such as 5-5.5 and with normal ammonium cation concentration (30-50 mM) fully reverses the change in the indicator color. On the contrary, a reaction of an indicator with urine at pH 5-8 and ammonium cation concentration above 60 mM changes the color of the indicator to a stable color.

An optional composition for the identification of dehydration is provided hereinbelow (Table 5), though this composition is applicable for other diagnostic uses as disclosed herein.

TABLE 5

Components of the dehydration indicating composition

| Chemical Name | Function | % W/W |
|---|---|---|
| Cellulose acetate; Cellulose acetate butyrate | Polymer | 58.3 |
| Hexamol | Plasticizer | 37.5 |
| tri-dodecylmethyl ammonium chloride (TDMAC) | Ion-balance reagent | 3.48 |
| Citric acid | Competitive reagent | 0.19 |
| Bromothymol blue (BTB) | Indicator 1 | 0.44 |
| Bromo cresol purple | Indicator 2 | 0.13 |

The composition described in Table 5 does not include wetting agent. This formulation combines two kinds of polymers: cellulose acetate and cellulose acetate butyrate—which have different hydrophobicity. In addition, this formulation combines signaling produced by two indicators for achieving improved color change and higher sensitivity.

Example 11

A Composition for the Identification of Vaginal Secretions Associated with Bacterial Vaginosis A composition for the identification of vaginal secretions associated with bacterial vaginosis containing biogenic

TABLE 4

| component | gr/2000 ml distilled $H_2O$ | gr/300 ml distilled $H_2O$ | gr/185 ml distilled $H_2O$ | gr/110 ml distilled $H_2O$ | gr/80 ml distilled $H_2O$ | gr/55 ml distilled $H_2O$ |
|---|---|---|---|---|---|---|
| Urea | 3.20 | 3.20 | 3.20 | 3.20 | 3.20 | 3.20 |
| $(NH_4)H_2PO_4$ | 0.153 | 0.153 | 0.153 | 0.153 | 0.153 | 0.153 |
| $(NH_4)_2HPO_4$ | 0.027 | 0.027 | 0.027 | 0.027 | 0.027 | 0.027 |
| $CaCl_2 \cdot 2H_2O$ | 0.184 | 0.184 | 0.184 | 0.184 | 0.184 | 0.184 |
| $MgCl_2 \cdot 6H_2O$ | 0.130 | 0.130 | 0.130 | 0.130 | 0.130 | 0.130 |
| $Na_2SO_4$ | 0.122 | 0.122 | 0.122 | 0.122 | 0.122 | 0.122 |
| KCl | 1.76 | 1.76 | 1.76 | 1.76 | 1.76 | 1.76 |
| Specific Gravity via refractometer | 1.002 | 1.008 | 1.014 | 1.020 | 1.025 | 1.035 | amines, such as trimethylamine, 1,4-diaminobutane and 1,5-diamino pentane, comprises cellulose acetate in an amount of 34.6%; dibutylphthalate in an amount of 25.8%; 2-ethoxy ethanol in an amount of 32.2%; tri-dodecylmethyl ammonium chloride (Aliquat 336) in an amount of 4.7%; nitrazine yellow in an amount of 0.6%; and citric acid in an amount of 2.2%; wherein the percents are weight percent based on the total weight of the composition and the total weight of the composition equals 100% (Table 6).

TABLE 6

Components of the vaginal secretions indicating composition

| Function | % W/W | Chemical |
| --- | --- | --- |
| Polymer | 34.60 | Cellulose Acetate |
| Plasticizer | 25.80 | Dibutylphthalate |
| Ion-balance reagent | 4.70 | Aliquat 336 |
| Wetting agent | 32.20 | 2-Ethoxy Ethanol |
| Indicator | 0.60 | Nitrazine Yellow |
| Competitive reagent | 2.20 | Citric Acid |

The method for preparation of an article for the identification of vaginal secretions associated with bacterial vaginosis comprising the steps of:
Step 1: To 85.98 ml of acetone add 3.61 g cellulose acetate, 2.58 ml dibutylphthalate, 0.55 ml Aliquat, 3.61 ml 2-Ethoxy ethanol, 0.46 g citric acid and 0.06 g nitrazine yellow dissolved in 3.61 ml DDW.
Step 2: Stir the mixture for few minutes to complete dissolving.
Step 3: Coat a polyester non-woven fabric with the polymer solution to yield the desired product.
Step 4: Dry over night.

Example 12

A Composition for the Detection of Amniotic Fluid without Urine Interference

The composition for the detection of amniotic fluid without urine interference comprising cellulose acetate in an amount of 34.2%; dibutylphthalate in an amount of 25.5%; 2-ethoxy ethanol in an amount of 31.8%; Aliquat 336 in an amount of 4.6%; nitrazine yellow in an amount of 0.5%; and tartaric acid in an amount of 3.4%; wherein the percents are weight percent based on the total weight of the composition and the total weight of the composition equals 100% (Table 7).

TABLE 7

Components of the amniotic fluid detecting composition

| Function | % W/W | Chemical |
| --- | --- | --- |
| Polymer | 34.20 | Cellulose Acetate |
| Plasticizer | 25.50 | Dibutylphthalate |
| Ion-balance reagent | 4.60 | Aliquat 336 |
| Wetting agent | 31.80 | 2-Ethoxy Ethanol |
| Indicator | 0.50 | Nitrazine Yellow |
| Competitive reagent | 3.40 | Tartaric Acid |

The method for preparation of an article for the identification of amniotic fluid without urine interference comprising the steps of:
Step 1: To 89.6 ml of acetone add 2.7 g cellulose acetate, 1.9 ml dibutylphthalate, 0.4 ml Aliquat 336, 2.7 ml 2-ethoxy ethanol, 0.4 g tartaric acid and 0.04 g nitrazine yellow dissolved in 2.7 ml DDW.
Step 2: Stir the mixture for few minutes to complete dissolving.
Step 3: Coat a polyester non-woven fabric with the polymer solution to yield the desired product.
Step 4: Dry over night.

Example 13

Method for Preparation of Vaginal Secretion-Monitoring Swab

A composition for the preparation of vaginal secretion monitoring swab for the detection of biogenic amines such as trimethylamine, 1,4-diamino butane and 1,5-diamino pentane, comprises cellulose acetate in an amount of 36.2%; dioctylphthalate in an amount of 25.4%; 2-ethoxy ethanol in an amount of 33.7%; tri-dodecylmethyl ammonium chloride (TDMAC) in an amount of 2.4%; nitrazine yellow in an amount of 0.6%; and citric acid in an amount of 1.6%; wherein the percents are weight percent based on the total weight of the composition and the total weight of the composition equals 100% (Table 8).

TABLE 8

Components of the vaginal secretion-monitoring swab

| Function | % W/W | Chemical |
| --- | --- | --- |
| Polymer | 36.26 | Cellulose Acetate |
| Plasticizer | 25.39 | Dioctylphthalate |
| Ion-balance reagent | 2.41 | TDMAC |
| Wetting agent | 33.73 | 2-Ethoxy Ethanol |
| Indicator | 0.58 | Nitrazine Yellow |
| Competitive reagent | 1.63 | Citric Acid |

The method for the preparation of vaginal secretion monitoring swab comprising the steps of:
Step 1: To 80.5 ml of acetone add 0.8 g cellulose acetate, 0.6 ml dioctylphthalate, 0.05 ml tri-dodecylmethyl ammonium chloride (TDMAC), 0.8 ml 2-ethoxy ethanol, 0.9 g citric acid and 0.01 g nitrazine yellow dissolved in 0.8 ml DDW.
Step 2: Stir the mixture for few minutes to complete dissolving.
Step 3: Coat a swab with tip made of polyester fabric with the polymer solution to yield the desired product.
Step 4: Dry over night.
The tip may be prepared by using a short strip, rolled on the stick of the swab, or by coating the tip of an integrated swab, where the tip consists of any screening fabric.
The composition is applied to the swab for example by dipping the swab in the composition or by spraying or spreading the composition onto the swab. The swab with the applied composition is allowed to dry. When dry, the indicator is bound to the substrate with the help of the polymer.

Example 14

A Composition for the Detection of Elevated pH Values in Vaginal Secretions without Urine Interference A composition for the detection of elevated pH values in vaginal secretions comprises cellulose acetate (polymer); dioctylphthalate (plasticizer); 2-ethoxy ethanol (volatile wetting agent); tri-dodecylmethyl ammonium chloride (TDMAC; ion-balance reagent); nitrazine yellow (indicator); and citric acid (competitive agent) is formed wherein the ion balance reagent to indicator ration is 7:1 (Table 9). The pH level spans from 4.5 to 7.0 for the acetic acid at concentration threshold of 7.6 µg/ml or higher, and pH 6.0 for lactic acid at concentration threshold of 6.6 µg/ml or higher. Clearly, the any organic acid can be used in the composition for any urine remains.

TABLE 9

Components of the vaginal secretion detecting composition

| Function | % W/W | Chemical |
|---|---|---|
| Polymer | 44 | Cellulose Acetate |
| Plasticizer | 27 | Dioctylphthalate |
| Ion-balance reagent | 3 | TDMAC |
| Wetting agent | 25 | 2-Ethoxy Ethanol |
| Indicator | 0.5 | Nitrazine Yellow |
| Competitive reagent | 0.4 | Citric Acid |

The method for preparation of an article for the identification of vaginal secretions, containing organic acids with a pH level of 5.0 or higher includes mixing all of the components listed in Table 8 with 10 ml of acetone; stirring the mixture for few minutes for complete dissolution; coating a polyester non-woven fabric with the polymer solution to yield the desired product; and drying the resulting article over night.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention. Thus the expressions "means to . . . " and "means for . . . ," or any method step language, as may be found in the specification above and/or in the claims below, followed by a functional statement, are intended to define and cover whatever chemical structure, or whatever function, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A method of identifying a pathological condition in a female subject which comprises:
    positioning a secretion-monitoring article to receive a biological fluid secreted from the subject, the secretion-monitoring article comprising a body that includes an absorbent material for absorbing the biological fluid and an indicator system having a hydrophobic chemical composition comprising at least one indicator agent and at least one ion-balance reagent which is a quaternary amine, wherein the indicator system provides an indication of physiological conditions associated with a pH or a buffer capacity of the biological fluid, which indication is stable and remains indicative for at least 48 hours; and
    viewing the article within the at least 48 hour period to identify the pathological condition based on the indication determined by the indicator system,
    wherein the at least one ion-balance reagent and the at least one indicator agent are present in amounts sufficient to provide a molar ratio that is within the range of 3:1 to 10:1.

2. The method of claim 1, wherein the at least one ion-balance reagent is in an amount of about 1% to 6% and the at least one indicator agent is in an amount of about 0.1% to 2%, wherein the percents are weight percent based on the total weight of the composition and the total weight of the composition equals 100%.

3. The method of claim 1, wherein the indicator system further comprises a pre-formed polymer and a plasticizer.

4. The method of claim 3, wherein the indicator system further comprises a wetting agent.

5. The method of claim 4, wherein the wetting agent is selected from the group consisting of: triethylene glycol, ethylene glycol, sorbitol and 2-ethoxy ethanol and combinations thereof.

6. The method of claim 4, wherein pre-formed polymer is in an amount of about 30% to 50%; the plasticizer is in an amount of about 20% to 30%; the wetting agent is in an amount of about 20% to 35%; the at least one ion-balance reagent is in an amount of about 1% to 6% and the at least one indicator agent is in an amount of about 0.1% to 2%, wherein the percents are weight percent based on the total weight of the composition and the total weight of the composition equals 100%.

7. The method of claim 6, wherein the pre-formed polymer is in an amount of about 33% to 45%; the plasticizer is in an amount of about 24% to 28%; the wetting agent is in an amount of about 24% to 34%; the at least one ion-balance reagent is in an amount of about 2% to 5% and the at least one indicator agent is in an amount of about 0.3% to 1%, wherein the percents are weight percent based on the total weight of the composition and the total weight of the composition equals 100%.

8. The method of claim 3, wherein the pre-formed polymer comprises one or more polymer selected from the group consisting of: a weakly acidic polyelectrolyte polymer, cellulose, sodium carboxymethyl cellulose, ethyl cellulose, nitrocellulose or cellulose acetate.

9. The method of claim 3, wherein the plasticizer is selected from the group consisting of: castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl) adipate, bis-(2-ethylhexyl) sebacate and dibutylphthalate and combinations thereof.

10. The method of claim 1, wherein the indicator system further comprises a competitive reagent for establishing a pre-set threshold of an analyte of interest in the biological fluid, the competitive reagent having the same charge as the at least one indicator reagent wherein the binding affinity of the competitive reagent to the analyte is stronger than the binding affinity of the at least one indicator reagent to said analyte, and wherein the concentration of the competitive reagent determines a pre-set threshold of a visible indication such that upon contact of the composition with a bodily fluid comprising said analyte in a concentration above the pre-set threshold, said composition provides an indication of physiological conditions associated with the pH or the buffer capacities of the bodily fluid.

11. The method of claim 10, wherein the competitive reagent is in an amount of about 0.2% to 8%, wherein the percents are weight percent based on the total weight of the composition and the total weight of the composition equals 100%.

12. The method of claim 10, wherein the competitive reagent is selected from the group consisting of: citric acid, oxalic acid, tartaric acid, succinic acid, glutaric acid, lactic acid, pyruvic acid, hydroxypropionic acid, hydroxyvaleric acid, adipic acid, suberic acid, orotic acid, phthalic acid, 2-[(2-hydroxy-1,1-bis(hydroxymethyl)ethyl)amino]ethanesulfonic acid, 4-(2-hydroxyethyl)piperazine-1-ethanesulfonic acid, cyclodextrine sulfate, dextran sulfate, and carboxymethyl cellulose.

13. The method of claim 1, wherein the biological fluid has a pH, and the indicator agent has a pKa that is lower than the pH of the biological fluid, wherein the indicator system determines a pH which is evidence of the pathological condition.

14. The method of claim 1, wherein the indicator agent is negatively charged.

15. The method of claim 14, wherein the at least one indicator agent is selected from the group consisting of: cresol red, alizarin, bromcresol purple, chlorophenol red, nitrazine yellow, bromthymol blue bromoxylenol blue, neutral red, phenol red, thymol blue, xylenol blue and m-cresol purple and combinations thereof.

16. The method of claim 1, wherein the at least one ion-balance reagent is selected from the group consisting of: di(alkyl)dimethyl ammonium chloride, N-methyl-N,N-bis(alkanoyl oxyethyl)-N-(2-hydroxyethyl) ammonium methylsulfate, vinylbenzyl dimethylcocoammonium chloride, methyl trioctyl ammonium chloride tricaprylylmethyl ammonium chloride, tridodecylmethyl ammonium chloride and cetyltrimethyl ammonium chloride and combinations thereof.

17. The method of claim 1, wherein the pathological condition is selected from the group consisting of bacterial vaginosis, the presence of amniotic fluid, hydration and Candida.

18. The method of claim 1, wherein the indicator system reversibly changes color when contacted by normal urine.

19. The method of claim 1, further comprising drying the indicator system and removing the indicator system from the article prior to the viewing step.

20. The method of claim 1, further comprising
providing a color-encoding chart comprising a plurality of color codes and a description of medical condition for each color code; and
comparing the color of said indication to the color-encoding chart and interpreting thereby determining the medical condition.

* * * * *

UNITED STATES PATENT AND TRADEMARK OFFICE
CERTIFICATE OF CORRECTION

PATENT NO. : 7,947,467 B2  Page 1 of 1
APPLICATION NO. : 12/472653
DATED : May 24, 2011
INVENTOR(S) : Kritzman et al.

It is certified that error appears in the above-identified patent and that said Letters Patent is hereby corrected as shown below:

Title Page:
Item (63) Related U.S. Application Data, after "PCT/IL02/00588, filed on Jul. 18, 2002" delete ", which" and insert -- . Application No. 12/472,653 --; and after "Sep. 28, 2006, now abandoned" delete ", and" and insert -- . Application No. 10/285,449 is --.

The related U.S. Application Data will correctly appear as follows:

Item (63) Continuation-in-part of application No. 11/949,541, filed on Dec. 3, 2007, now Pat. No. 7,541,177, which is a continuation of application No. 11/105,438, filed on Apr. 14, 2005, now Pat. No. 7,314,752, which is a continuation-in-part of application No. 10/285,499, filed on Nov. 1, 2002, now Pat. No. 6,921,647, which is a continuation-in-part of application No. PCT/IL02/00588, filed on Jul. 18, 2002. Application No. 12/472,653 is a continuation of application No. 11/541,198, filed on Sep. 28, 2006, now abandoned. Application No. 10/285,499 is a continuation-in-part of application No. 09/907,926, filed on Jul. 19, 2001, now Pat. No. 6,627,394.

Signed and Sealed this
Twelfth Day of July, 2011

David J. Kappos
*Director of the United States Patent and Trademark Office*